(12) United States Patent
Min

(10) Patent No.: US 9,314,510 B2
(45) Date of Patent: Apr. 19, 2016

(54) HUMAN LAMININ α2 CHAIN LG3 DOMAIN AND ACTIVE PEPTIDES PROMOTING CELL ADHESION, SPREADING, MIGRATION, AND NEURITE OUTGROWTH

(75) Inventor: Byung-Moo Min, Seoul (KR)

(73) Assignee: SNU R&DB Foundation, Seoul (KR)

( * ) Notice: Subject to any disclaimer, the term of this patent is extended or adjusted under 35 U.S.C. 154(b) by 118 days.

(21) Appl. No.: 13/418,137

(22) Filed: Mar. 12, 2012

(65) Prior Publication Data

US 2012/0238503 A1    Sep. 20, 2012

(30) Foreign Application Priority Data

Mar. 15, 2011    (KR) ................. 10-2011-0022946

(51) Int. Cl.

| | | |
|---|---|---|
| *G01N 33/567* | (2006.01) | |
| *A01N 1/00* | (2006.01) | |
| *C12N 5/077* | (2010.01) | |
| *C12N 5/0775* | (2010.01) | |
| *C12N 5/0789* | (2010.01) | |
| *A61K 35/28* | (2015.01) | |
| *A61K 35/30* | (2015.01) | |
| *A61K 38/39* | (2006.01) | |

(52) U.S. Cl.
CPC ..................................... *A61K 38/39* (2013.01)

(58) Field of Classification Search
CPC ............. C07K 14/789; C07K 2319/00; C07K 14/70546; A61K 38/00; A61K 38/39; C12N 5/0622; C12N 2502/08; C12N 5/0619; C12N 2533/52; G01N 2333/78; G01N 2500/10; G01N 33/5058; G01N 33/5023; G01N 33/5026; G01N 33/5029; G01N 33/5044; G01N 33/68; C08L 89/009
See application file for complete search history.

(56) References Cited

U.S. PATENT DOCUMENTS

| 6,632,790 B1 * | 10/2003 | Yurchenco ................. 514/21.2 |
| 2007/0141652 A1 * | 6/2007 | Zheng et al. ................. 435/7.23 |

FOREIGN PATENT DOCUMENTS

| WO | WO 9111462 A2 * | 8/1991 | ............. A61K 37/02 |
| WO | WO 9508628 A2 * | 3/1995 | ............. C12N 15/12 |
| WO | WO 9919348 A9 * | 4/1999 | ............. C07K 14/00 |

OTHER PUBLICATIONS

Blight Nat. Neurosci. 2002. 5: 1051-4.*
Schmidt et al. Annu. Rev. Biomed. Eng. 2003. 5: 293-347.*
Hoke et al. Nat. Clin. Pract. Neurol. 2006: 448-454.*
Barry et al. J. Cell Sci. 1994. 107: 2033-2045.*
Richardson et al., Nature. 1996, 380: 538-540.*
Renaudin et al. J. Neurosci. Res. 1999, 55: 458-471.*
Zhang et al. The EMBO J. 2006, 25: 5284-529.*
Schober et al. J. Cell Biol.2007, 176: 667-680.*
Aplin, A. E., et al. (1998), Signal Transduction and Signal Modulation by Cell Adhesion Receptors: The Role of Integrins, Cadherins, Immunoglobulin-Cell Adhesion Molecules, and Selectins, *Pharmacol. Rev.*, vol. 50, No. 2, pp. 197-263.
Barry, S. T., et al. (1994), "The RhoA-dependent assembly of focal adhesions in Swiss 3T3 cells is associated with increased tyrosine phosphorylation and the recruitment of both pp125FAK and protein kinase C-δ to focal adhesions," *J. Cell Sci.*, 107, 2033-2045.
Biernaskie, J. A. et al. (2006), "Isolation of skin-derived precursors (SKPs) and differentiation and enrichment of their Schwann cell progeny," *Nat. Protoc.*, vol. 1 No. 6, 2803-2812.
Carafoli, F., et al. (2009), Crystal Structure of the LG1-3 Region of the Laminin α2 Chain*, *J. Biol. Chem.*, vol. 284, No. 34, pp. 22786-22792.
Clark, E. A., et al. (1995) Integrins and Signal Transduction Pathways: The Road Taken, *Science*, vol. 268, pp. 233-239.
Colognato, H. et al. (2000), "Form and Function: The Laminin Family of Heterotrimers," *Developmental Dynamics* 218:213-234.
Jung, S. Y, et al. (2009), "A Biologically Active Sequence of the Laminin α2 Large Globular 1 Domain Promotes Cell Adhesion through Syndecan-1 by Inducing Phosphorylation and Membrane Localization of Protein Kinase Cδ," *J. Biol. Chem.*, vol. 284, No. 46, pp. 31764-31775.
Disatnik, M. H., et al., (2002) Sequential activation of individual PKC isozymes in integrin-mediated muscle cell spreading: a role for MARCKS in an integrin signaling pathway. *J. Cell Sci.*, 115, 2151-2163.
Dovas, A., et al. (2006), PKCα-dependent activation of RhoA by syndecan-4 during focal adhesion formation, *J. Cell Sci.*, 119, 2837-2846.
Hall, H., et al. (2003), N-terminal α-dystroglycan binds to different extracellular matrix molecules expressed in regenerating peripheral nerves in a proteinmediated manner and promotes neurite extension of PC12 cells, *Mol. Cell. Neurosci.*, 24:1062-1073.
Hohenester, E., et al. (1999), The Crystal Structure of a Laminin G-like Module Reveals the Molecular Basis of α-Dystroglycan Binding to Laminins, Perlecan, and Agrin, Mol. Cell, vol. 4, 783-792.
Huang, X., et al. (1998), The integrin αvβ6 is critical for keratinocyte migration on both its known ligand, fibronectin, and on vitronectin, *J. Cell Sci.*, 111, 2189-2195.
Hynes, R. O. (1992), Integrins: Versatility, Modulation, and Signaling in Cell Adhesion, *Cell*, vol. 69, 11-25.

(Continued)

*Primary Examiner* — Chang-Yu Wang
(74) *Attorney, Agent, or Firm* — Lathrop & Gage LLP

(57) ABSTRACT

The present invention relates to human laminin α2 chain LG3 domain and active peptides promoting cell adhesion, spreading, migration, and neurite outgrowth. More particularly, it was found that when nerve cells are incubated using human laminin α2 chain LG3 domain and active peptides in the LG3 domain, cell adhesion, spreading, migration, and neurite outgrowth of nerve cells promote and the promotion of cell adhesion, spreading, migration, and neurite outgrowth of nerve cells are integrin-mediated and achieved by the activation of PKCδ and FAK phosphorylation. Thus, the present invention can be very useful for researches on cell adhesion, spreading, migration, and neurite outgrowth activities of cells which are focused on nerve cells and mediated by various extracellular matrix proteins including laminin, manufacture of artificial nerve conduits, burns treatment, wounds treatment, and tissue regeneration.

7 Claims, 18 Drawing Sheets

(56) References Cited

OTHER PUBLICATIONS

Jaken, S., et al. (1989), "Association of Type 3 Protein Kinase C with Focal Contacts in Rat Embryo Fibroblasts," *J. Cell Biol.*, vol. 109, 697-704.

Katoh, K., et al. (2007), "Rho-kinase dependent organization of stress fibers and focal adhesions in cultured fibroblasts," *Genes Cells*, 12, 623-638.

Kim, J. M., et al. (2005), The PPFLMLLKGSTR motif in globular domain 3 of the human laminin-5 α3 chain is crucial for integrin α3β1 binding and cell adhesion, *Exp. Cell Res.*, 304: 317-327.

Kim, J. M., et al. (2007), Vacuolar-type $H^+$-ATPase-mediated acidosis promotes in vitro osteoclastogenesis via modulation of cell migration, *Int. J. Mol. Med.*, 19: 393-400.

Leivo, I. et al. (1988), "Merosin, a protein specific for basement membranes of Schwann cells, striated muscle, and trophoblast, is expressed late in nerve and muscle development," *Proc. Natl. Acad. Sci. USA*, vol. 85, pp. 1544-1548.

Lewis, J. M., et al. (1996), "Protein Kinase C Regulates αvβ5-dependent Cytoskeletal Associations and Focal Adhesion Kinase Phosphorylation," *J. Cell Biol.*, 134, No. 5, 1323-1332.

Liu, S., et al. (2000), "Integrin cytoplasmic domain-binding proteins," *J. Cell Sci.*, 113, 3563-3571.

Miranti, C. K., et al. (1999), "Protein Kinase C Regulates Integrin-induced Activation of the Extracellular Regulated Kinase Pathway Upstream of She," *J. Biol. Chem.*, vol. 274, No. 15, Issue of Apr. 9, pp. 10571-10581.

Nomizu, M. et al. (1996), "Active peptides from the carboxyl-terminal globular domain of laminin α2 and *Drosophila* α chains," FEBS Letters 396, 37-42.

Richard, B. L. (1996), "Identification of Synthetic Peptides Derived from Laminin α1 and α2 Chains with Cell Type Specificity for Neurite Outgrowth," Experimental Cell Research 228, 98-105, Article No. 0304.

Richardson, A., et al. (1996), A mechanism for regulation of the adhesion-associated protein tyrosine kinase $pp125^{FAK}$, *Nature*, vol. 380, pp. 538-540.

Ron, D., et al. (1999), "New insights into the regulation of protein kinase C and novel phorbol ester receptors," *FASEB J.*, 13, 1658-1676.

Schlaepfer, D. D., et al. (1998), Integrin signaling and tyrosine phosphorylation: just the FAKs? *Trends Cell Biol.*, vol. 8, pp. 151-157.

Schwartz, M. A., et al. (1995), "Integrins: Emerging Paradigms of Signal Transduction," *Annu. Rev. Cell Dev. Biol.*, 11:549-99.

Smirnov, S. P., et al. (2002), "Contributions of the LG Modules and Furin Processing to Laminin-2 Functions," *J. Biol. Chem.*, vol. 277, No. 21, Issue of May 24, pp. 18928-18937.

Suzuki, N., et al. (2005), "Functional Sites in the Laminin Alpha Chains," *Connect. Tissue Res.*, 6:142-152.

Tomaselli, K. J., et al. (1990), A Neuronal Cell line (PC12) Expresses Two $β_1$,—Class Integrins- $α_1β_1$ and $α_3β_1$—That Recognize Different Neurite Outgrowth-Promoting Domains in Laminin, *Neuron*, vol. 5, 651-662.

Vossmeyer, D., et al. (2002), Phospholipase Cγ Binds $α_1β_1$ Integrin and Modulates $α_1β_1$ Integrin-specific Adhesion, *J. Biol. Chem.*, vol. 277, No. 7, Issue of Feb. 15, pp. 4636-4643.

Woods, A., et al. (1992), "Protein kinase C involvement in focal adhesion formation," *J. Cell Sci.*, 101, 277-290.

\* cited by examiner

Fig. 5A

| Peptide | Sequence | |
|---|---|---|
| Ln2-LG3-P2 | RNIPPFEGCIWN | (SEQ ID NO: 1) |
| Ln2-LG3-P2-DN1 | NIPPFEGCIWN | (SEQ ID NO: 35) |
| Ln2-LG3-P2-DN2 | IPPFEGCIWN | (SEQ ID NO: 36) |
| Ln2-LG3-P2-DN3 | PPFEGCIWN | (SEQ ID NO: 37) |
| Ln2-LG3-P2-DN4 | PFEGCIWN | (SEQ ID NO: 38) |
| Ln2-LG3-P2-DN5 | FEGCIWN | (SEQ ID NO: 39) |
| Ln2-LG3-P2-DC1 | RNIPPFEGCIW | (SEQ ID NO: 40) |
| Ln2-LG3-P2-DC2 | RNIPPFEGCI | (SEQ ID NO: 41) |
| Ln2-LG3-P2-DC3 | RNIPPFEGC | (SEQ ID NO: 42) |
| Ln2-LG3-P2-DN3-DC1 | PPFEGCIW | (SEQ ID NO: 43) |
| Ln2-LG3-P2-DN3-DC2 | PPFEGCI | (SEQ ID NO: 44) |
| Ln2-LG3-P2-DN3-DC3 | PPFEGC | (SEQ ID NO: 45) |
| Ln2-LG3-P2-DN3-DC4 | PPFEG | (SEQ ID NO: 46) |
| Ln2-LG3-P2-DN3-DC5 | PPFE | (SEQ ID NO: 47) |
| Ln2-LG3-P2-DN3-DC6 | PPF | (SEQ ID NO: 48) |
| Ln2-LG3-P2-AC1 | RNIPPFEGCIWNLVINSVPMDFAR | (SEQ ID NO: 49) |
| Ln2-LG3-P2-AC2 | RNIPPFEGCIWNLVINSVPMDFARPVSFKNADIGRC | (SEQ ID NO: 50) |

SEQUENCE LISTING

<160> NUMBER OF SEQ ID NOS: 50

<210> SEQ ID NO 1

```
<211> LENGTH: 12
<212> TYPE: PRT
<213> ORGANISM: Homo sapiens

<400> SEQUENCE: 1

Arg Asn Ile Pro Pro Phe Glu Gly Cys Ile Trp Asn
1               5                   10

<210> SEQ ID NO 2
<211> LENGTH: 209
<212> TYPE: PRT
<213> ORGANISM: Homo sapiens

<400> SEQUENCE: 2

Val Glu Leu Ser Pro Val Pro Ile Asp Val Gly Thr Glu Ile Asn Leu
1               5                   10                  15

Ser Phe Ser Thr Lys Asn Glu Ser Gly Ile Ile Leu Leu Gly Ser Gly
            20                  25                  30

Gly Thr Pro Ala Pro Pro Arg Arg Lys Arg Arg Gln Thr Gly Gln Ala
        35                  40                  45

Tyr Tyr Val Ile Leu Leu Asn Arg Gly Arg Leu Glu Val His Leu Ser
    50                  55                  60

Thr Gly Ala Arg Thr Met Arg Lys Ile Val Ile Arg Pro Glu Pro Asn
65                  70                  75                  80

Leu Phe His Asp Gly Arg Glu His Ser Val His Val Glu Arg Thr Arg
                85                  90                  95

Gly Ile Phe Thr Val Gln Val Asp Glu Asn Arg Arg Tyr Met Gln Asn
            100                 105                 110

Leu Thr Val Glu Gln Pro Ile Glu Val Lys Lys Leu Phe Val Gly Gly
        115                 120                 125

Ala Pro Pro Glu Phe Gln Pro Ser Pro Leu Arg Asn Ile Pro Pro Phe
    130                 135                 140

Glu Gly Cys Ile Trp Asn Leu Val Ile Asn Ser Val Pro Met Asp Phe
145                 150                 155                 160

Ala Arg Pro Val Ser Phe Lys Asn Ala Asp Ile Gly Arg Cys Ala His
                165                 170                 175

Gln Lys Leu Arg Glu Asp Glu Asp Gly Ala Ala Pro Ala Glu Ile Val
            180                 185                 190

Ile Gln Pro Glu Pro Val Pro Thr Pro Ala Phe Pro Thr Pro Thr Pro
        195                 200                 205

Val

<210> SEQ ID NO 3
<211> LENGTH: 20
<212> TYPE: DNA
<213> ORGANISM: Artificial Sequence
<220> FEATURE:
<223> OTHER INFORMATION: LG1-1 forward primer

<400> SEQUENCE: 3
aaacaagcca attctatcaa                                           20

<210> SEQ ID NO 4
<211> LENGTH: 19
<212> TYPE: DNA
<213> ORGANISM: Artificial Sequence
<220> FEATURE:
<223> OTHER INFORMATION: LG1-1 reward primer

<400> SEQUENCE: 4
```

```
atttccattt cccatcatt                                                  19

<210> SEQ ID NO 5
<211> LENGTH: 23
<212> TYPE: DNA
<213> ORGANISM: Artificial Sequence
<220> FEATURE:
<223> OTHER INFORMATION: LG1 forward primer

<400> SEQUENCE: 5
gccactcgag caggaggtga ctg                                             23

<210> SEQ ID NO 6
<211> LENGTH: 28
<212> TYPE: DNA
<213> ORGANISM: Artificial Sequence
<220> FEATURE:
<223> OTHER INFORMATION: LG1 reward primer

<400> SEQUENCE: 6
gccaccatgg tcaactgaca gtgcatcc                                        28

<210> SEQ ID NO 7
<211> LENGTH: 23
<212> TYPE: DNA
<213> ORGANISM: Artificial Sequence
<220> FEATURE:
<223> OTHER INFORMATION: LG2 forward primer

<400> SEQUENCE: 7
gccactcgag cagtcctcag gtg                                             23

<210> SEQ ID NO 8
<211> LENGTH: 32
<212> TYPE: DNA
<213> ORGANISM: Artificial Sequence
<220> FEATURE:
<223> OTHER INFORMATION: LG2 reward primer

<400> SEQUENCE: 8
gccaccatgg tcactccaca aaaccaggct ta                                   32

<210> SEQ ID NO 9
<211> LENGTH: 28
<212> TYPE: DNA
<213> ORGANISM: Artificial Sequence
<220> FEATURE:
<223> OTHER INFORMATION: LG3 forward primer

<400> SEQUENCE: 9
gccactcgag tgtggagctc tccctgt                                        28

<210> SEQ ID NO 10
<211> LENGTH: 32
<212> TYPE: DNA
<213> ORGANISM: Artificial Sequence
<220> FEATURE:
<223> OTHER INFORMATION: LG3 reward primer

<400> SEQUENCE: 10
gccaccatgg tcaaactggg gtgggcgtag ga                                   32

<210> SEQ ID NO 11
<211> LENGTH: 30
<212> TYPE: DNA
```

<210> SEQ ID NO 11
<211> LENGTH: 30
<212> TYPE: DNA
<213> ORGANISM: Artificial Sequence
<220> FEATURE:
<223> OTHER INFORMATION: LG4 forward primer

<400> SEQUENCE: 11
gccactcgag tctgacacat ggtccttgtg                                30

<210> SEQ ID NO 12
<211> LENGTH: 30
<212> TYPE: DNA
<213> ORGANISM: Artificial Sequence
<220> FEATURE:
<223> OTHER INFORMATION: LG4 reward primer

<400> SEQUENCE: 12
gccaccatgg tcatgcaaaa catgtcccaa                                30

<210> SEQ ID NO 13
<211> LENGTH: 29
<212> TYPE: DNA
<213> ORGANISM: Artificial Sequence
<220> FEATURE:
<223> OTHER INFORMATION: LG5 forward primer

<400> SEQUENCE: 13
gccactcgag tgcaaatgct cagaggggga                                29

<210> SEQ ID NO 14
<211> LENGTH: 37
<212> TYPE: DNA
<213> ORGANISM: Artificial Sequence
<220> FEATURE:
<223> OTHER INFORMATION: LG5 reward primer

<400> SEQUENCE: 14
gccaccatgg tcacctgggg ttacacttat ttttatt                        37

<210> SEQ ID NO 15
<211> LENGTH: 12
<212> TYPE: PRT
<213> ORGANISM: Artificial Sequence
<220> FEATURE:
<223> OTHER INFORMATION: Ln2-LG3-P1

<400> SEQUENCE: 15

Phe Gln Pro Ser Pro Leu Arg Asn Ile Pro Pro Phe
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Ln2-LG3-P3

<400> SEQUENCE: 16

Lys Asn Ala Asp Ile Gly Arg Cys Ala His Gln Lys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Ln2-LG3-P4

<400> SEQUENCE: 17

```
Arg Cys Ala His Gln Lys Leu Arg Glu Asp Glu Asp
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Ln2-LG3-P5

<400> SEQUENCE: 18

Leu Arg Glu Asp Glu Asp Gly Ala Ala Pro Ala Glu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Ln2-LG3-P6

<400> SEQUENCE: 19

Glu Gly Cys Ile Trp Asn Leu Val Ile Asn Ser Val
1               5                   10

<210> SEQ ID NO 20
<211> LENGTH: 12
<212> TYPE: PRT
<213> ORGANISM: Artificial Sequence
<220> FEATURE:
<223> OTHER INFORMATION: scrambled peptide

<400> SEQUENCE: 20

Asn Trp Glu Ile Arg Cys Ile Pro Gly Asn Pro Phe
1               5                   10

<210> SEQ ID NO 21
<211> LENGTH: 12
<212> TYPE: PRT
<213> ORGANISM: Artificial Sequence
<220> FEATURE:
<223> OTHER INFORMATION: rLG3-M1

<400> SEQUENCE: 21

Ala Asn Ile Pro Pro Phe Glu Gly Cys Ile Trp Asn
1               5                   10

<210> SEQ ID NO 22
<211> LENGTH: 12
<212> TYPE: PRT
<213> ORGANISM: Homo sapiens

<400> SEQUENCE: 22

Arg Asn Ile Pro Pro Phe Glu Gly Cys Ile Trp Asn
1               5                   10

<210> SEQ ID NO 23
<211> LENGTH: 12
<212> TYPE: PRT
<213> ORGANISM: Mus musculus

<400> SEQUENCE: 23

Arg Asn Ile Pro Ala Phe Gln Gly Cys Val Trp Asn
1               5                   10
```

```
<210> SEQ ID NO 24
<211> LENGTH: 12
<212> TYPE: PRT
<213> ORGANISM: Rattus norvegicus

<400> SEQUENCE: 24

Arg Asn Ile Pro Ala Phe Gln Gly Cys Val Trp Asn
1               5                   10

<210> SEQ ID NO 25
<211> LENGTH: 12
<212> TYPE: PRT
<213> ORGANISM: Gallus gallus

<400> SEQUENCE: 25

Arg Asn Ile Pro Pro Phe Glu Gly Cys Ile Trp Asn
1               5                   10

<210> SEQ ID NO 26
<211> LENGTH: 12
<212> TYPE: PRT
<213> ORGANISM: Apis mellifera

<400> SEQUENCE: 26

Arg Val Asn Val Pro Phe Gln Gly Cys Ile Trp Asn
1               5                   10

<210> SEQ ID NO 27
<211> LENGTH: 12
<212> TYPE: PRT
<213> ORGANISM: Danio rerio

<400> SEQUENCE: 27

Arg Pro Ser Val Pro Phe Glu Gly Cys Ile Trp Asn
1               5                   10

<210> SEQ ID NO 28
<211> LENGTH: 12
<212> TYPE: PRT
<213> ORGANISM: Homo sapiens

<400> SEQUENCE: 28

Thr Met Arg Arg Ser Phe His Gly Cys Ile Lys Asn
1               5                   10

<210> SEQ ID NO 29
<211> LENGTH: 12
<212> TYPE: PRT
<213> ORGANISM: Mus musculus

<400> SEQUENCE: 29

Lys Met Arg Thr Ser Phe His Gly Cys Ile Lys Asn
1               5                   10

<210> SEQ ID NO 30
<211> LENGTH: 12
<212> TYPE: PRT
<213> ORGANISM: Rattus norvegicus

<400> SEQUENCE: 30

Arg Met Arg Thr Ser Phe His Gly Cys Ile Lys Asn
1               5                   10

<210> SEQ ID NO 31
<211> LENGTH: 12
```

```
<212> TYPE: PRT
<213> ORGANISM: Equus caballus

<400> SEQUENCE: 31

Arg Met Arg Gly Ser Phe His Gly Cys Ile Arg Asn
1               5                   10

<210> SEQ ID NO 32
<211> LENGTH: 12
<212> TYPE: PRT
<213> ORGANISM: Canis lupus

<400> SEQUENCE: 32

Lys Met Arg Lys Ser Phe His Gly Cys Ile Lys Asn
1               5                   10

<210> SEQ ID NO 33
<211> LENGTH: 12
<212> TYPE: PRT
<213> ORGANISM: Gallus gallus

<400> SEQUENCE: 33

Lys Met Thr Gly Ser Phe Tyr Gly Cys Ile Ser Asn
1               5                   10

<210> SEQ ID NO 34
<211> LENGTH: 12
<212> TYPE: PRT
<213> ORGANISM: Danio rerio

<400> SEQUENCE: 34

Thr Leu Thr Pro Ala Phe Tyr Gly Cys Ile Arg Asn
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Ln2-LG3-P2-DN1

<400> SEQUENCE: 35

Asn Ile Pro Pro Phe Glu Gly Cys Ile Trp Asn
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Ln2-LG3-P2-DN2

<400> SEQUENCE: 36

Ile Pro Pro Phe Glu Gly Cys Ile Trp Asn
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Ln2-LG3-P2-DN3

<400> SEQUENCE: 37

Pro Pro Phe Glu Gly Cys Ile Trp Asn
1               5
```

```
<210> SEQ ID NO 38
<211> LENGTH: 8
<212> TYPE: PRT
<213> ORGANISM: Artificial Sequence
<220> FEATURE:
<223> OTHER INFORMATION: Ln2-LG3-P2-DN4

<400> SEQUENCE: 38

Pro Phe Glu Gly Cys Ile Trp Asn
1               5

<210> SEQ ID NO 39
<211> LENGTH: 7
<212> TYPE: PRT
<213> ORGANISM: Artificial Sequence
<220> FEATURE:
<223> OTHER INFORMATION: Ln2-LG3-P2-DN5

<400> SEQUENCE: 39

Phe Glu Gly Cys Ile Trp Asn
1               5

<210> SEQ ID NO 40
<211> LENGTH: 11
<212> TYPE: PRT
<213> ORGANISM: Artificial Sequence
<220> FEATURE:
<223> OTHER INFORMATION: Ln2-LG3-P2-DC1

<400> SEQUENCE: 40

Arg Asn Ile Pro Pro Phe Glu Gly Cys Ile Trp
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Ln2-LG3-P2-DC2

<400> SEQUENCE: 41

Arg Asn Ile Pro Pro Phe Glu Gly Cys Ile
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Ln2-LG3-P2-DC3

<400> SEQUENCE: 42

Arg Asn Ile Pro Pro Phe Glu Gly Cys
1               5

<210> SEQ ID NO 43
<211> LENGTH: 8
<212> TYPE: PRT
<213> ORGANISM: Artificial Sequence
<220> FEATURE:
<223> OTHER INFORMATION: Ln2-LG3-P2-DN3-DC1

<400> SEQUENCE: 43

Pro Pro Phe Glu Gly Cys Ile Trp
1               5
```

<210> SEQ ID NO 44
<211> LENGTH: 7
<212> TYPE: PRT
<213> ORGANISM: Artificial Sequence
<220> FEATURE:
<223> OTHER INFORMATION: Ln2-LG3-P2-DN3-DC2

<400> SEQUENCE: 44

Pro Pro Phe Glu Gly Cys Ile
1               5

<210> SEQ ID NO 45
<211> LENGTH: 6
<212> TYPE: PRT
<213> ORGANISM: Artificial Sequence
<220> FEATURE:
<223> OTHER INFORMATION: Ln2-LG3-P2-DN3-DC3

<400> SEQUENCE: 45

Pro Pro Phe Glu Gly Cys
1               5

<210> SEQ ID NO 46
<211> LENGTH: 5
<212> TYPE: PRT
<213> ORGANISM: Artificial Sequence
<220> FEATURE:
<223> OTHER INFORMATION: Ln2-LG3-P2-DN3-DC4

<400> SEQUENCE: 46

Pro Pro Phe Glu Gly
1               5

<210> SEQ ID NO 47
<211> LENGTH: 4
<212> TYPE: PRT
<213> ORGANISM: Artificial Sequence
<220> FEATURE:
<223> OTHER INFORMATION: Ln2-LG3-P2-DN3-DC5

<400> SEQUENCE: 47

Pro Pro Phe Glu
1

<210> SEQ ID NO 48
<211> LENGTH: 3
<212> TYPE: PRT
<213> ORGANISM: Artificial Sequence
<220> FEATURE:
<223> OTHER INFORMATION: Ln2-LG3-P2-DN3-DC6

<400> SEQUENCE: 48

Pro Pro Phe
1

<210> SEQ ID NO 49
<211> LENGTH: 24
<212> TYPE: PRT
<213> ORGANISM: Artificial Sequence
<220> FEATURE:
<223> OTHER INFORMATION: Ln2-LG3-P2-AC1

<400> SEQUENCE: 49

Arg Asn Ile Pro Pro Phe Glu Gly Cys Ile Trp Asn Leu Val Ile Asn
1               5                   10                  15

Ser Val Pro Met Asp Phe Ala Arg

```
                          20

<210> SEQ ID NO 50
<211> LENGTH: 36
<212> TYPE: PRT
<213> ORGANISM: Artificial Sequence
<220> FEATURE:
<223> OTHER INFORMATION: Ln2-LG3-P2-AC2

<400> SEQUENCE: 50

Arg Asn Ile Pro Pro Phe Glu Gly Cys Ile Trp Asn Leu Val Ile Asn
1               5                   10                  15

Ser Val Pro Met Asp Phe Ala Arg Pro Val Ser Phe Lys Asn Ala Asp
            20                  25                  30

Ile Gly Arg Cys
            35
```

HUMAN LAMININ α2 CHAIN LG3 DOMAIN AND ACTIVE PEPTIDES PROMOTING CELL ADHESION, SPREADING, MIGRATION, AND NEURITE OUTGROWTH

CROSS-REFERENCES TO RELATED APPLICATION

This patent application claims the benefit of priority from Korean Patent Application 10-2011-0022946, filed on Mar. 15, 2011, the contents of which are incorporated herein by reference.

BACKGROUND OF THE INVENTION

1. Field of the Invention

The present disclosure relates to a domain promoting cell adhesion, spreading, migration, and neurite outgrowth and active peptides thereof, more particularly, to human laminin-2 α2 chain LG3 domain promoting cell adhesion, spreading, migration, and neurite outgrowth, and active peptides in the LG3 domain.

2. Description of the Related Art

Integrins are transmembrane adhesive receptors that mediate cell-cell and cell-extracellular matrix (ECM) interactions (Hynes, R. O. *Cell,* 1992). Integrin-mediated cell adhesion has been shown to regulate intracellular signaling pathways that orchestrate many cellular functions, such as proliferation, differentiation, survival, and migration (Clark, E. A., et al, *Science,* 1995). Signals from within the cell can modulate the integrin affinity and avidity for its ECM ligands, leading to changes in cell adhesion and migration ("inside-out" signaling) (Schwartz, M. A., et al, *Annu. Rev. Cell Dev. Biol.,* 1995; Hynes, R. O. *Cell,* 1992). Conversely, the binding of integrins to ECM proteins triggers a signal transduction cascade, so-called "outside-in" signaling (Schwartz, M. A., et al, *Annu. Rev. Cell Dev. Biol.,* 1995; Hynes, R. O. *Cell,* 1992), through its cytoplasmic domain that associates with focal adhesion kinase (FAK), Src-family kinases, and cytoskeleton-associated proteins, such as vinculin, talin, and paxillin (Liu, S., et al., *J. Cell Sci.,* 2000). Engagement of integrins by ligands induces activation of a number of intracellular signaling pathways, including mitogen-activated protein kinases, Rho family GTPases, phosphatidylinositol 3-kinase (PI3K), and protein kinase C (PKC) (Schlaepfer, D. D., et al., *Trends Cell Biol.,* 1998; Aplin, A. E., et al., *Pharmacol. Rev.,* 1998).

PKC is an important regulator of integrin-mediated signaling and cellular behavior, such as cell adhesion, spreading, migration, and focal adhesion formation (Woods, A., et al., *J. Cell Sci.,* 1992; Lewis, J. M., et al., *J. Cell Biol.,* 1996). The PKC family consists of at least 12 isoforms, which can be classified into three subfamilies base upon their primary structure (Ron, D., et al., *FASEB J.,* 1999): the conventional PKC isoforms PKCα, βI, βII and γ which are activated by calcium and diacylglycerol; the novel PKC isoforms, PKCδ, ε, η, θ, and μ that are activated by diacylglycerol but not by calcium; and the atypical PKC isoforms, PKC and t/A which are unresponsive to either diacylglycerol or calcium.

PKC activation by phorbol myristate acetate has been shown to induce the adhesion, spreading, and migration of cells (Huang, X., et al., *J. Cell Sci.,* 1998). PKC inhibition by pharmacological reagents inhibits cell adhesion and spreading as well as focal adhesion formation and FAK phosphorylation (Woods, A., et al., *J. Cell Sci.,* 1992; Disatnik, M. H., et al., *J. Cell Sci.,* 2002). Several PKC isoforms have been identified in the regulation of cellular behavior. For example, PKCε activation is involved in inducing muscle cell adhesion to fibronectin, and PKCα and δ mediate cell spreading (Disatnik, M. H., et al., *J. Cell Sci.,* 2002). PKCδ is recruited to focal adhesions in fibroblast adhesion to fibronectin, and PKCα has been localized to focal adhesions in rat embryo fibroblasts (Barry, S. T., et al., *J. Cell Sci.,* 1994; Jaken, S., et al., *J. Cell Biol.,* 1989). However, the mechanism of PKC activation in integrin-mediated intracellular adhesion, migration, spreading, and activities is not well understood.

Laminins are a family of basement membrane glycoproteins that has been shown to regulate a diverse array of biological activities, such as cell adhesion, spreading, migration, neurite outgrowth, tumor metastasis, angiogenesis, differentiation, and wound healing (Colognato, H., et al., *Dev. Dyn,* 2000). Laminins are composed of α, β, and γ polypeptide chains. The laminin α2 chain, a component of laminin-2 (α2β1γ1), laminin-4 (α2β2γ1), and laminin-12 (α2β1γ3), is expressed in skeletal and cardiac muscles, peripheral nerves, brain, and placenta (Leivo, I., et al., *Proc. Natl. Acad. Sci. USA,* 1988). The α chains contain a C-terminal large globular (LG) domain consisting of five globular modules (LG1-LG5) (Colognato, H., et al., *Dev. Dyn,* 2000). These have been known to bind integrins, α-dystroglycan, and syndecans, and be implicated as active regions for various biological functions. However, the receptor-binding motifs within LG domains of human laminin α2 chain and their biological functions and downstream signaling pathways are poorly understood.

Thus, the present inventors have performed research to identify an active motif within the human laminin α2 which is related to biological activities such as cell adhesion, spreading, migration, etc., thus identified that among five domains composing human laminin α2 chain, LG3 domain protein is involved in integrin-mediated cell adhesion, spreading, migration, and neurite outgrowth, and synthesized amino acids composing LG3 domain to measure biological activities, thus identified that a RNIPPFEGCIWN (SEQ ID NO:1) motif at position 2675 to 2686 in human laminin α2 chain is involved in promoting cell adhesion, spreading, migration, and neurite outgrowth and the integrin-mediated cell adhesion is achieved through the membrane recruitment of PKCδ and FAK phosphorylation at Tyr-397, thereby leading to completion of the present invention.

SUMMARY OF THE INVENTION

One object of the present invention is to identify human laminin α2 chain LG3 domain promoting nerve cell adhesion, spreading, migration, and neurite outgrowth and an active peptide in the domain, and to provide a pharmacological composition for nerve regeneration comprising the domain or peptide.

In order to achieve the object, the present invention provides a method of promoting cell adhesion, spreading, migration, growth, or regeneration in an individual, comprising administering a polypeptide or peptide to the individual, in which the polypeptide may include human laminin-2 α2 chain large globular (LG) 3 domain sequence, and the peptide may be an active peptide included in the human laminin-2 α2 chain large globular (LG) 3 domain sequence and consisting of one amino acid sequence selected from the group consisting of SEQ ID NOs: 1 and 35 to 50.

Furthermore, the present invention provides a pharmacological composition for nerve regeneration comprising a polypeptide comprising human laminin-2 α2 chain large globular (LG) 3 domain sequence.

The present invention also provides a pharmacological composition for nerve regeneration comprising a peptide having the amino acid sequence represented by SEQ ID NO:1, as an active peptide in human laminin-2 α2 chain large globular (LG) 3 domain sequence.

Furthermore, the present invention provides a pharmacological composition for nerve regeneration comprising a peptide having one amino acid sequence selected from the group consisting of SEQ ID NOs:35 to 50, as an active peptide in human laminin-2 α2 chain large globular (LG) 3 domain sequence.

The present invention also provides an agent for promoting nerve cell adhesion comprising human laminin-2 α2 chain large globular (LG) 3 domain or the active peptide in the domain.

Furthermore, the present invention provides a container for promoting nerve cell adhesion, spreading, migration, and neurite outgrowth, the container comprising human laminin-2 α2 chain large globular (LG) 3 domain or the active peptide in the domain.

The present invention also provides a method of promoting nerve cell adhesion, spreading, migration, and neurite outgrowth, the method comprising:

(1) fixing human laminin-2 α2 chain large globular (LG)$_3$ domain or the active peptide in the domain according to the present invention to a solid support; and (2) promoting nerve cell adhesion, spreading, migration, and neurite outgrowth at the solid support.

Furthermore, the present invention provides a therapeutic agent for treating burns or wounds, the agent comprising human laminin-2 α2 chain large globular (LG) 3 domain or the active peptide in the domain.

The present invention also provides an artificial nerve conduit or its scaffolds comprising human laminin-2 α2 chain large globular (LG) 3 domain or the active peptide in the domain.

Furthermore, the present invention provides a scaffold for tissue engineering comprising human laminin-2 α2 chain large globular (LG) 3 domain or the active peptide in the domain.

Human laminin α2 chain rLG domain (SEQ ID NO:2) and active peptides thereof (SEQ ID NOs:1, 35 to 50) according to the present invention have high biological activities such as cell adhesion, spreading, migration, and neurite outgrowth promotion and the nerve cell adhesion, spreading, migration, and neurite outgrowth promotive effects are achieved by the binding of the domain and peptides according to the present invention through the membrane recruitment of PKCδ and FAK phosphorylation at Tyr-397. Thus, the domain and peptides of the present invention can be very useful for cell adhesion activity research, burns treatment, wounds treatment, tissue regeneration using artificial nerve conduits or scaffolds thereof, etc.

BRIEF DESCRIPTION OF THE DRAWINGS

The above and other objects, features and other advantages of the present invention will be more clearly understood from the following detailed description taken in conjunction with the accompanying drawings.

FIG. 1A illustrates a schematic diagram of the human laminin α2 LG domains and their recombinant proteins;

FIG. 1B illustrates gel mobilities of purified rLG proteins treated with dithiothreitol (DTT) which were compared using SDS-PAGE;

FIG. 1C is a graph showing results of circular dichroism analyses of LG1, LG2, LG3, LG4, and LG5 domain proteins; and FIGS. 1D to 1F are graphs showing results of examining cell adhesion (1D), spreading (1E), and migration (1F) of PC12 cells on plates coated with laminin (5 μg/mL) or rLG1 to rLG5 proteins (25 μg/mL);

*: p<0.01 versus BSA-coated control.

Figure 2:
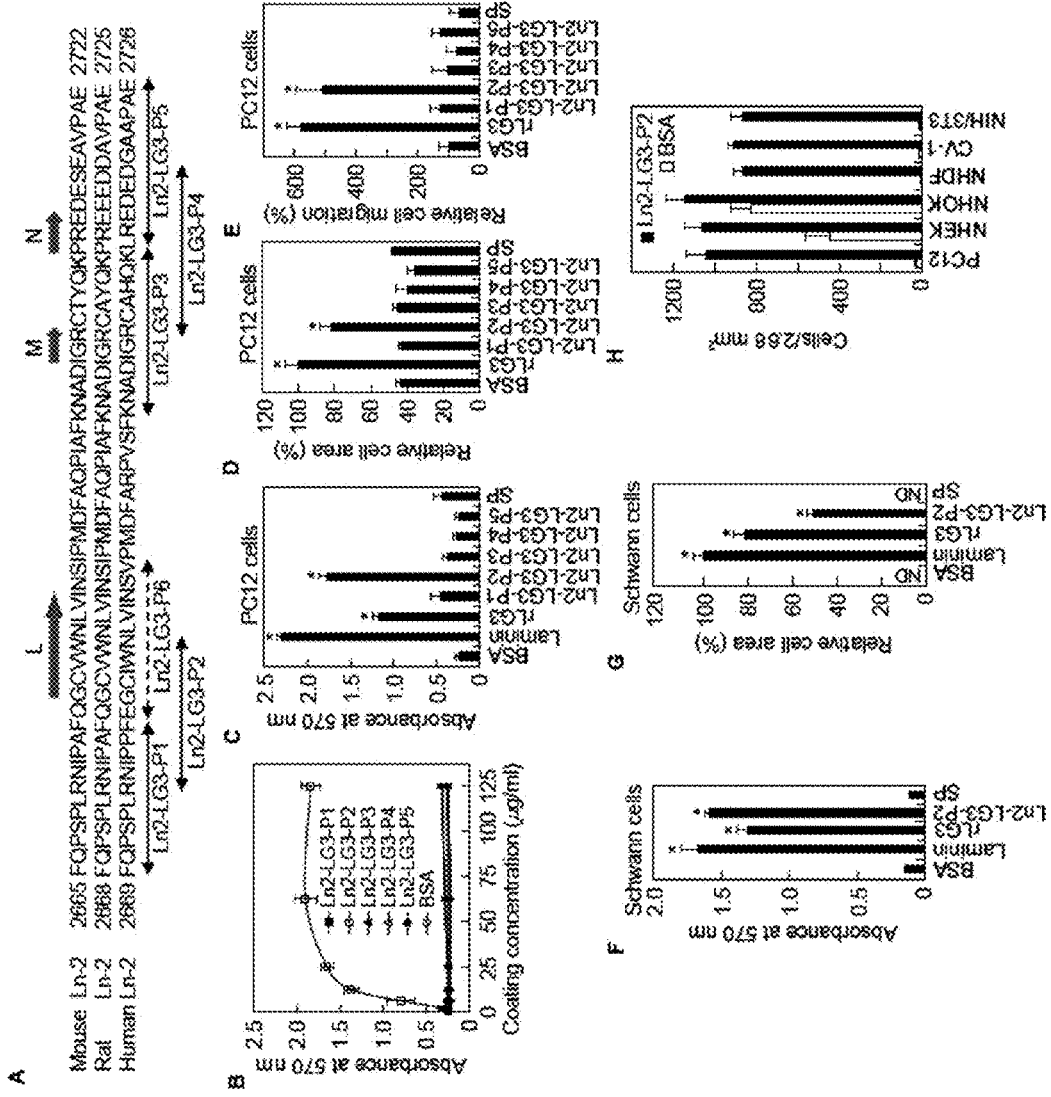

FIG. 2 is graphs showing that Ln2-LG3-P2 (SEQ ID NO:1, RNIPPFEGCIWN) within the LG3 domain promotes cell adhesion, spreading, and migration:

FIG. 2A is a diagram of amino acid sequence alignment of part of the laminin α2 LG3 domain from humans, rats, and mice;

FIG. 2B is a graph showing the dose-dependent cell adhesion of PC12 cells on plates coated with synthetic peptides;

■: the group coated with Ln2-LG3-P1 peptide;
□: the group coated with Ln2-LG3-P2 peptide;
▲: the group coated with Ln2-LG3-P3 peptide;
△: the group coated with Ln2-LG3-P4 peptide;
●: the group coated with Ln2-LG3-P5 peptide;
○: the group coated with BSA;

FIGS. 2C to 2E are graphs showing results of examining cell adhesion (2C), spreading (2D), and migration (2E) of PC12 cells on plates coated with laminin (5 μg/mL), rLG3(25 μg/mL), Ln2-LG3-P1 (62.5 μg/mL), Ln2-LG3-P2 (62.5 μg/mL), Ln2-LG3-P3 (62.5 μg/mL), Ln2-LG3-P4 (62.5 μg/mL), Ln2-LG3-P5 (62.5 μg/mL), and SP (Scrambled peptide, SEQ ID NO:20) (62.5 μg/mL);

FIGS. 2F and 2G are graphs showing results of examining cell adhesion (2F), and migration (2G) of Schwann cells on plates coated with laminin (5 μg/mL), rLG3(25 μg/mL), Ln2-LG3-P1 (62.5 μg/mL), Ln2-LG3-P2 (62.5 μg/mL), Ln2-LG3-P3 (62.5 μg/mL), Ln2-LG3-P4 (62.5 μg/mL), Ln2-LG3-P5 (62.5 μg/mL), and SP (Scrambled peptide, SEQ ID NO:20) (62.5 μg/mL);

*: p<0.01 versus BSA-coated control;

ND: not detected; and

FIG. 2H is a graph showing results of examining cell adhesion to Ln2-LG3-P2 in normal human epidermal keratinocytes (NHEK), normal human oral keratinocytes (NHOK), normal human dermal fibroblasts (NHDF), CV-1, and NIH/3T3 cells.

Figure 3:
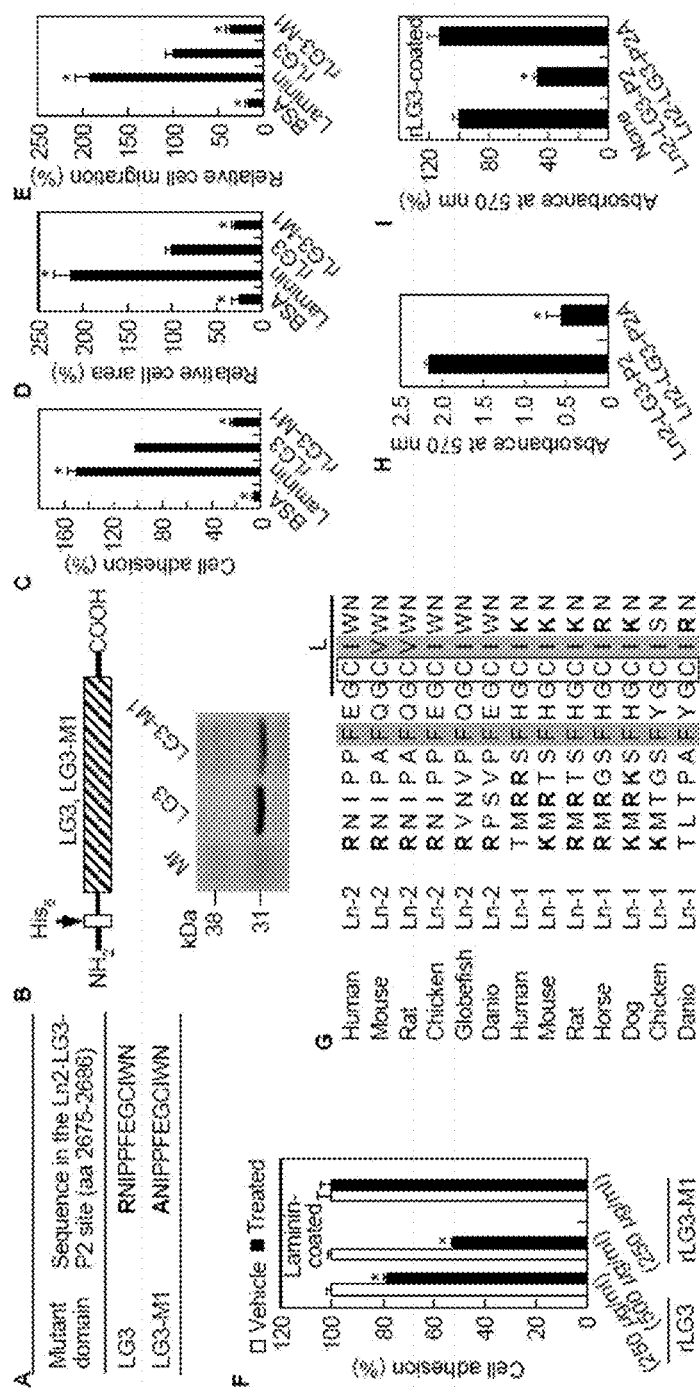

FIG. 3 is diagrams showing that the basic amino acid residue Arg in the Ln2-LG3-P2 peptide is important for functional activities of the Ln2-LG3-P2 peptide:

FIG. 3A shows a site-directed mutant domain of basic residue in the Ln2-LG3-P2 peptide of laminin α2 LG3 domain;

FIG. 3B is a schematic diagram and a diagram of SDS-PAGE analysis of the mutant rLG3 protein (rLG3-M1) expressed in which Arg in the P2 site of recombinant protein rLG3 was substituted to Ala;

FIG. 3C is graphs showing results of examining adhesion of PC12 cells on plates coated with laminin (5 μg/mL), rLG3 (25 μg/mL), and rLG3-M1 (25 μg/mL);

*: p<0.01;

FIG. 3D is graphs showing results of examining spreading of PC12 cells on plates coated with laminin (5 μg/mL), rLG3 (25 μg/mL), and rLG3-M1 (25 μg/mL);

*: p<0.01;

FIG. 3E is graphs showing results of examining migration of PC12 cells on plates coated with laminin (5 μg/mL), rLG3 (25 μg/mL), and rLG3-M1 (25 μg/mL);

*: p<0.01;

FIG. 3F is graphs showing results of examining inhibition of cell adhesion on plates coated with laminin (5 μg/mL) in which PC12 cells were pretreated with rLG3 (250 or 500 μg/mL), rLG3-M1 (250 μg/mL), or vehicle (phosphate buffer, pH 3.0) for 30 min;

*: p<0.01;

FIG. 3G is a comparative diagram of alignment of the Ln2-LG3-P2 sequences in laminin-1 and laminin-2 from several species;

FIG. 3H is a graph showing that cell adhesion of PC12 cells was inhibited on plates coated with Ln2-LG2-P2 (500 μg/mL) and Ln2-LG3-P2A (500 μg/mL);

*: p<0.01;

FIG. 3I is a graph showing results of examining adhesion of PC12 cells on plates coated with rLG3 (25 μg/mL) in which PC12 cells were pretreated with Ln2-LG2-P2 (500 μg/mL) and Ln2-LG3-P2A (500 μg/mL); and

*: p<0.01.

Figure 4:
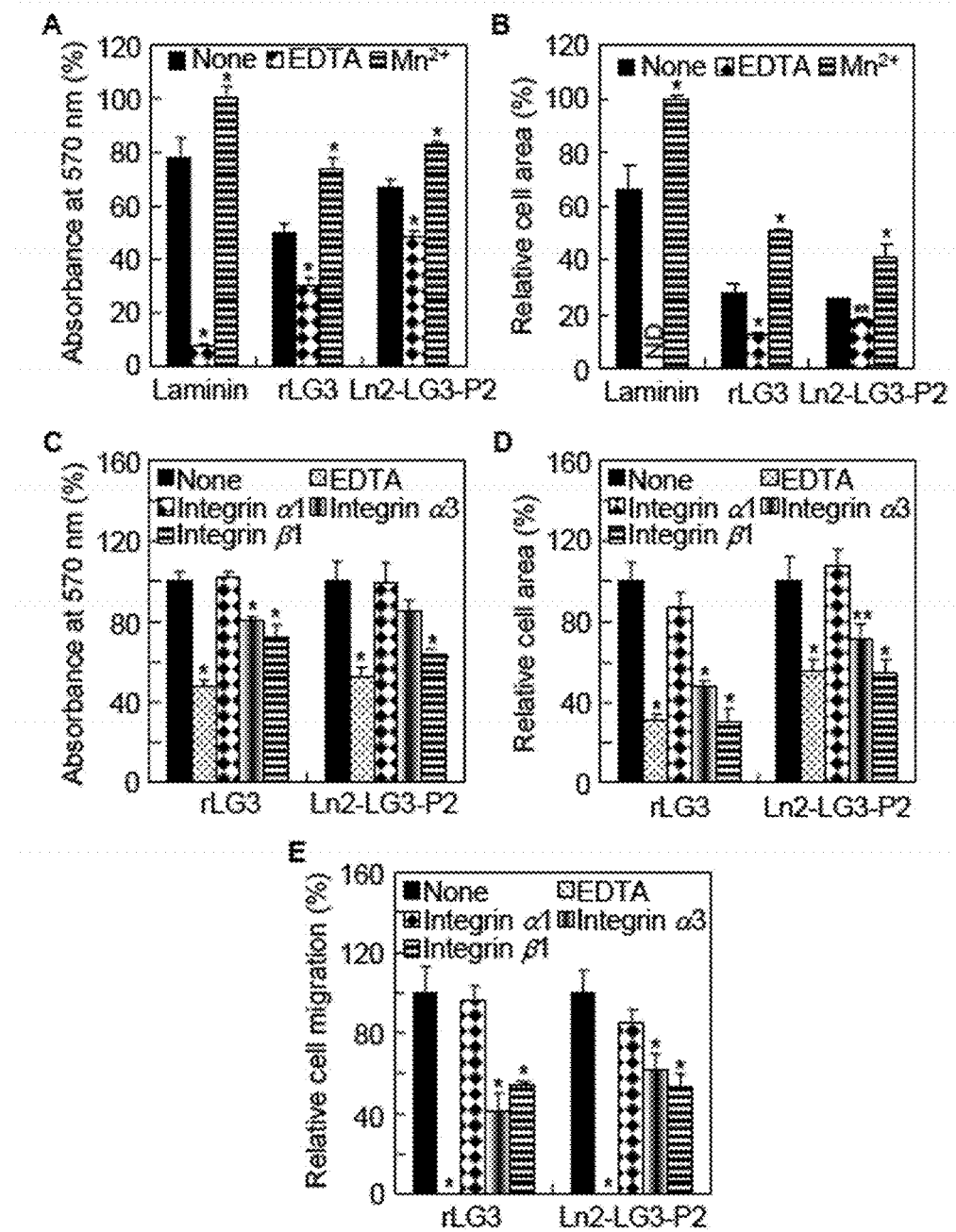

FIG. 4 is diagrams showing that cell adhesion, spreading, migration, and neurite outgrowth promoting activities of rLG3 and Ln2-LG3-P2 are mediated by integrin β1:

FIG. 4A and FIG. 4B are graphs showing results of examining cell adhesion (4A) and spreading (4B) to laminin, rLG3, and Ln2-LG3-P2 peptide in PC12 cells pretreated with 1 mM $MnCl_2$ or 5 mM EDTA;

■: PC12 cells pretreated without EDTA;

▶: PC12 cells pretreated with 5 mM EDTA;

▤: PC12 cells pretreated with 1 mM $MnCl_2$;

FIGS. 4C to 4E are graphs showing inhibition of cell adhesion (4C), spreading (4D), and migration (4E) to laminin, rLG3, and Ln2-LG3-P2 peptide in PC12 cells pretreated with 5 mM EDTA, 10 μg/mL integrin α3 and β1 antibodies;

■: PC12 cells pretreated without EDTA or integrin antibody;

⊡: a PC12 cells pretreated with 5 mM EDTA;

▶: PC12 cells pretreated with 10 μg/mL integrin α1 antibody;

⊞: PC12 cells pretreated with 10 μg/mL integrin α3 antibody;

▤: PC12 cells pretreated with 10 μg/mL integrin β1 antibody;

*: p<0.01; and

**: p<0.05.

Figure 5B:
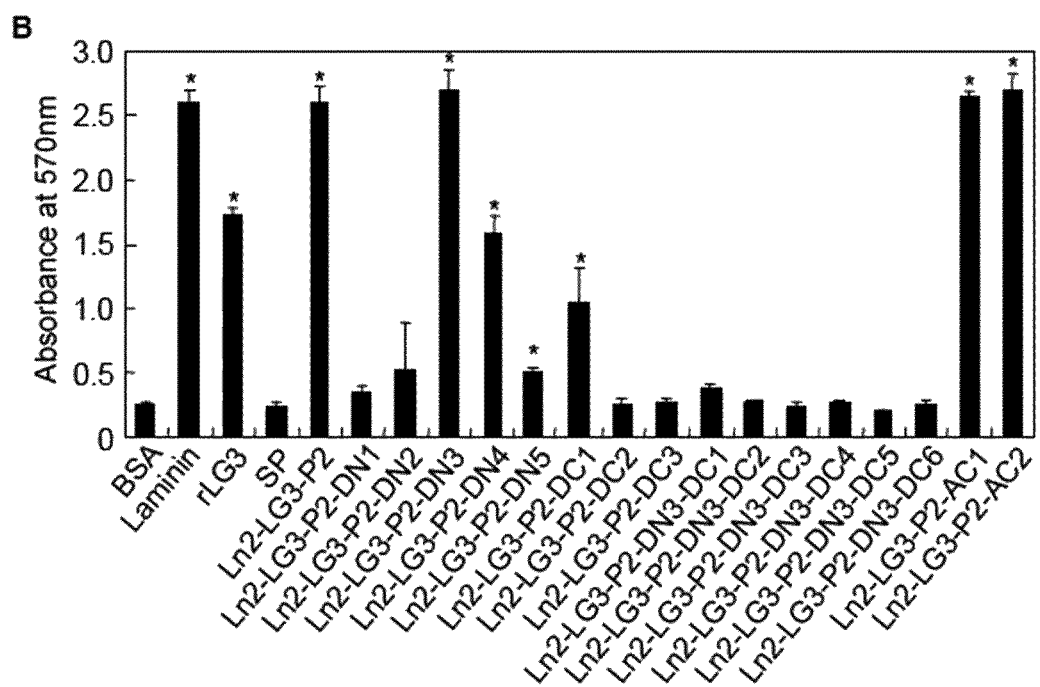
Figure 5C:
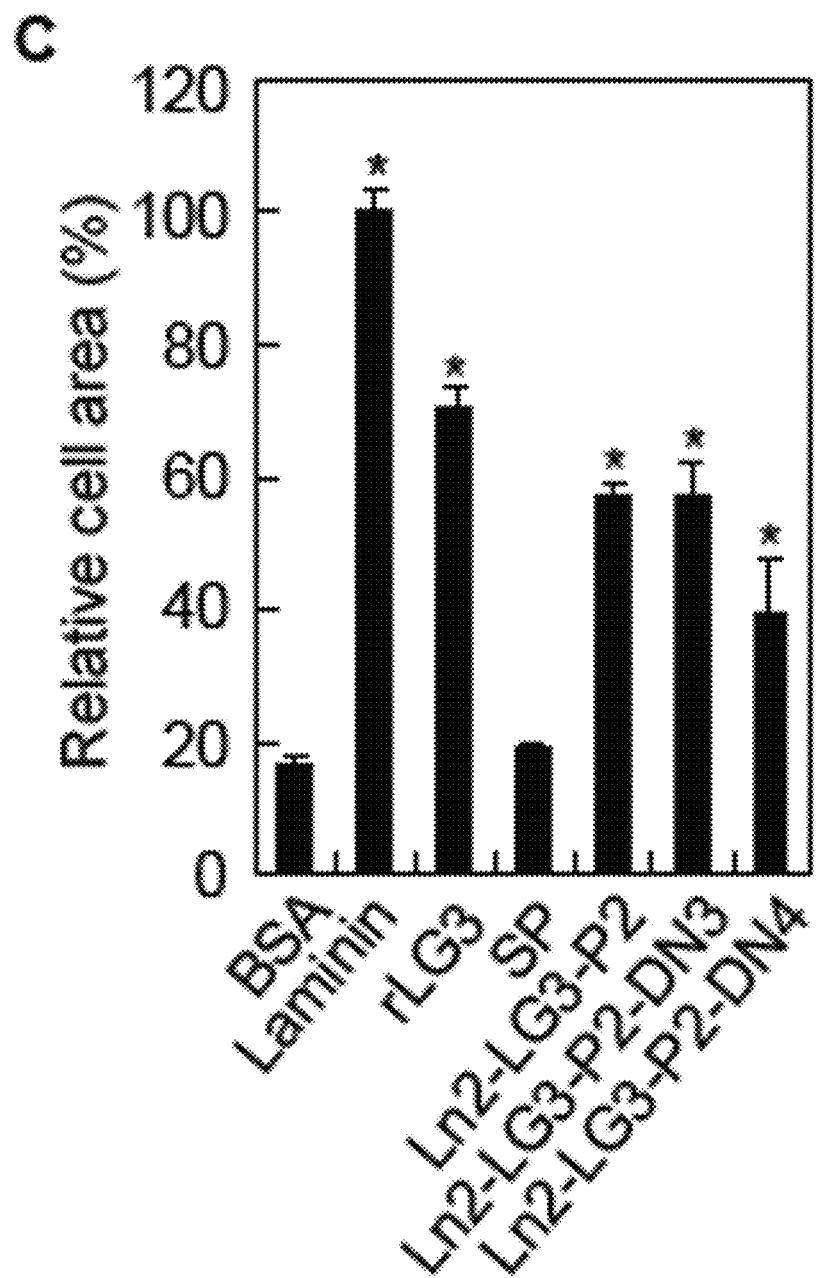
Figure 5D:
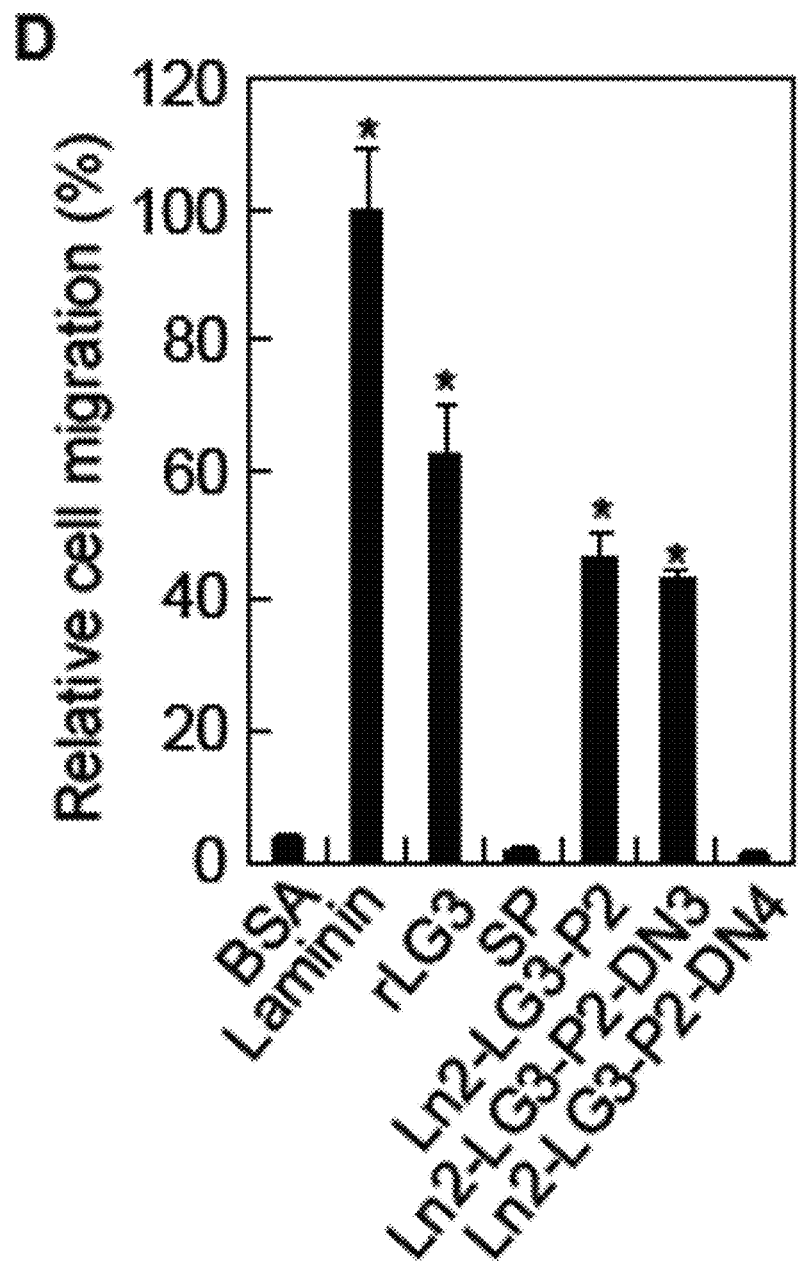

FIG. 5 shows results showing the effect of N- or C-terminal truncated peptides or of C-terminal added peptides of the Ln2-LG3-P2 peptide on cell adhesion, spreading, migration, and neurite outgrowth promotion:

FIG. 5A is a table showing amino acid sequence of N- or C-terminal truncated peptides or of C-terminal added peptides of the Ln2-LG3-P2 peptide;

FIG. 5B is a graph showing adhesion of PC12 cells to laminin (5 μg/mL), rLG3 (25 μg/mL) and peptides (62.5 μg/mL) described in FIG. 5A;

SP: scrambled peptide;

FIG. 5C and FIG. 5D show results of examining spreading (5C) and migration (5D) of PC12 cells to laminin (5 μg/mL), rLG3 (25 μg/mL), scrambled peptides (62.5 μg/mL), and Ln2-LG3-P2-DN3 (62.5 μg/mL), Ln2-LG3-P2-DN4 (62.5 μg/mL) described in FIG. 5A; and

*: p<0.01.

Figure 6:
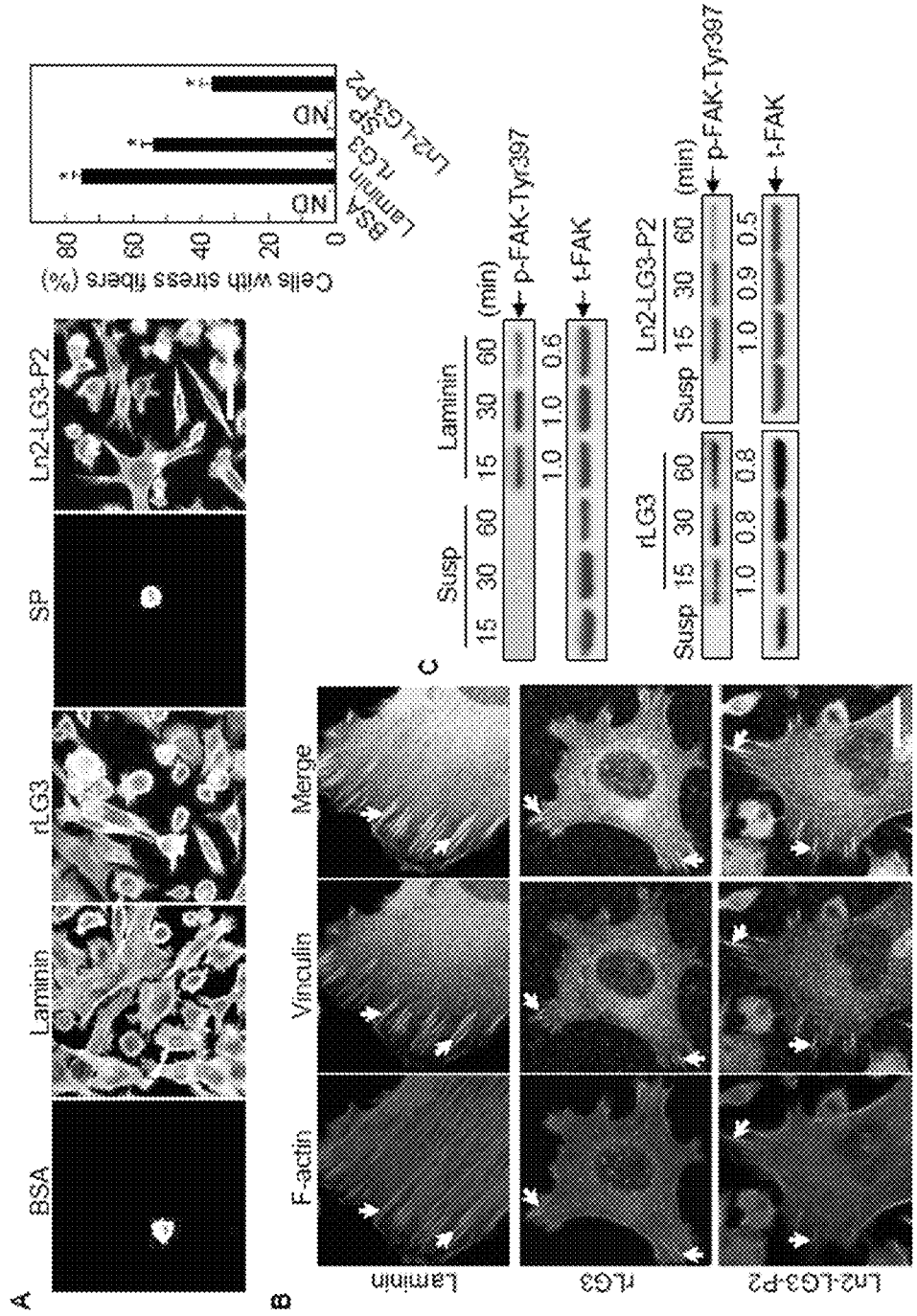

FIG. 6 shows results of examining stress fiber formation, focal adhesions, and FAK phosphorylation at Tyr-397 induced by rLG3 and Ln2-LG3-P2 peptide:

FIG. 6A is a diagram of F-actin in PC12 cells cultured on glass slide chambers coated with BSA, laminin, rLG3, scrambled peptide (SP), or Ln2-LG3-P2 observed by immunostaining;

ND: not detected;

—: 50 μm;

FIG. 6B is a diagram of F-actin and vinculin in PC12 cells cultured on glass slide chambers coated with laminin, rLG3, or Ln2-LG3-P2 observed by immunostaining;

↙: focal adhesions;

—: 20 μm;

FIG. 6B is a diagram of the extent of FAK phosphorylation in PC12 cells cultured on glass slide chambers coated with laminin, rLG3, or Ln2-LG3-P2 identified by western blotting;

Susp: suspension;

15 min: the group in which PC12 cells were cultured on glass slide chambers coated with laminin, rLG3, or Ln2-LG3-P2 for 15 min;

30 min: the group in which PC12 cells were cultured on glass slide chambers coated with laminin, rLG3, or Ln2-LG3-P2 for 30 min;

60 min: the group in which PC12 cells were cultured on glass slide chambers coated with laminin, rLG3, or Ln2-LG3-P2 for 60 min.

Figure 7:
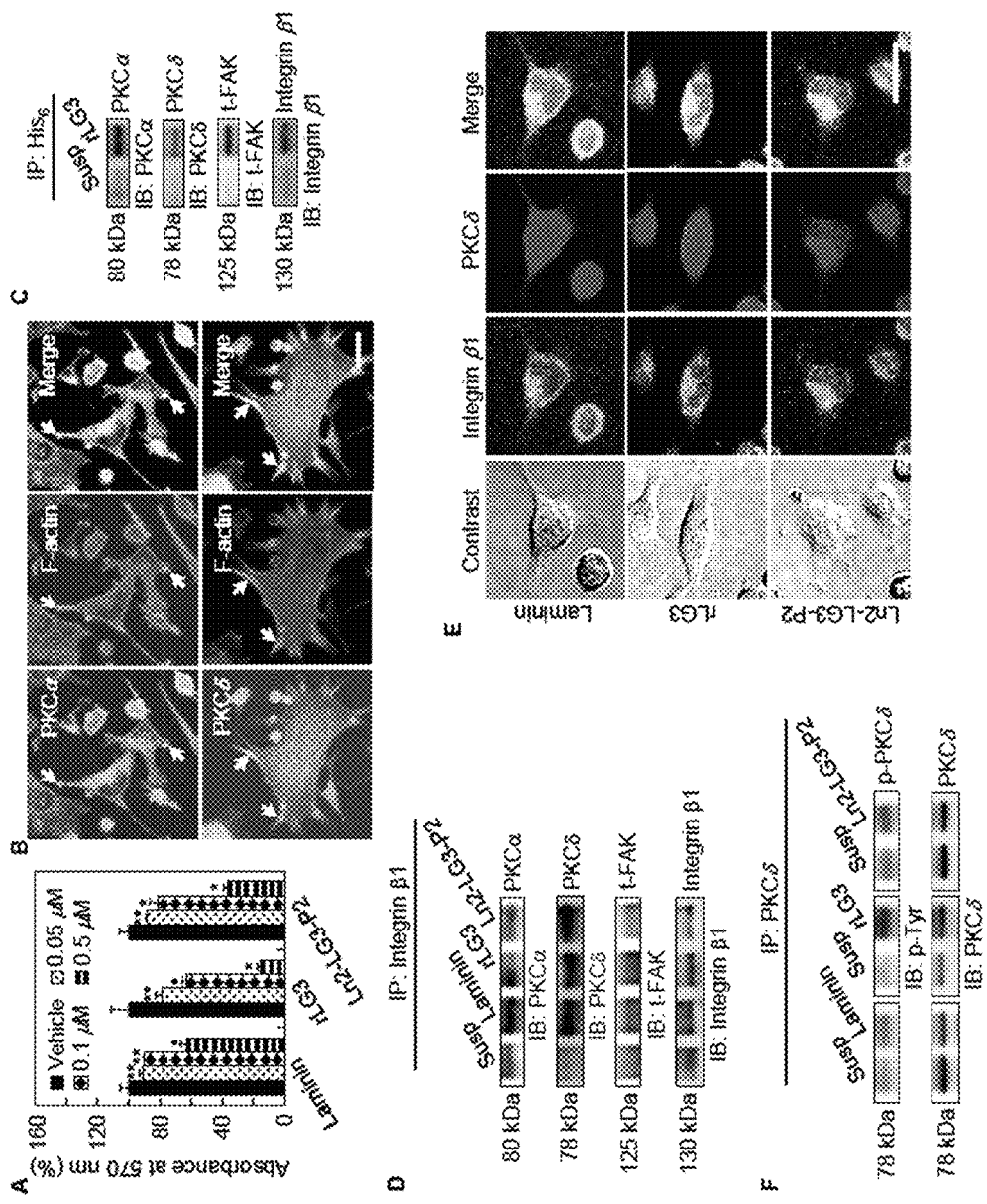

FIG. 7 is diagrams and a graph showing results of localization and tyrosine phosphorylation of PKCδ by rLG3 and Ln2-LG3-P2 peptide:

FIG. 7A is a graph showing that adhesion of PC12 cells to laminin, rLG3, and Ln2-LG3-P2 peptide were inhibited by calphostin C treatment;

*: p<0.01;

**: p<0.05;

■: vehicle (dimethylsulfoxide, DMSO);

⊡: 0.05 μM calphostin C treatment;

▶: 0.1 μM calphostin C treatment;

▤: 0.5 μM calphostin C treatment;

FIG. 7B is a diagram showing results of immunostaining PC12 cells plated on laminin-coated glass slides with the anti-PKCα or δ antibodies and rhodamine-phalloidin antibody;

↙: the ends of stress fibers;

—: 20 μm;

FIG. 7C is a diagram showing interactions of $His_6$-tagged rLG3 with PKCα, PKCδ, FAK, and integrin β1;

Susp: suspension;

FIG. 7D is a diagram of interactions of integrin β1 with PKCα, PKCδ, FAK, and integrin β1 in PC12 cells cultured on laminin-, rLG3- or Ln2-LG3-P2-coated dishes identified through immunoprecipitation using integrin β1;

Susp: suspension;

Laminin: PC12 cells cultured on laminin-coated dish;

rLG3: PC12 cells cultured on rLG3-coated dish;

Ln2-LG3-P2: PC12 cells cultured on Ln2-LG3-P2-coated dish;

FIG. 7E is a diagram of colocalization of PKCδ with integrin β1 in PC12 cells cultured on laminin-, rLG3- or Ln2-LG3-P2-coated dishes identified through immunostaining;

FIG. 7F is a diagram of interaction of PKCδ with phosphotyrosine in PC12 cells cultured on laminin-, rLG3-, or Ln2-LG3-P2-coated dishes;

Susp: suspension;

Laminin: PC12 cells cultured on laminin-coated dish;

rLG3: PC12 cells cultured on rLG3-coated dish;

Ln2-LG3-P2: PC12 cells cultured on Ln2-LG3-P2-coated dish.

Figure 8:
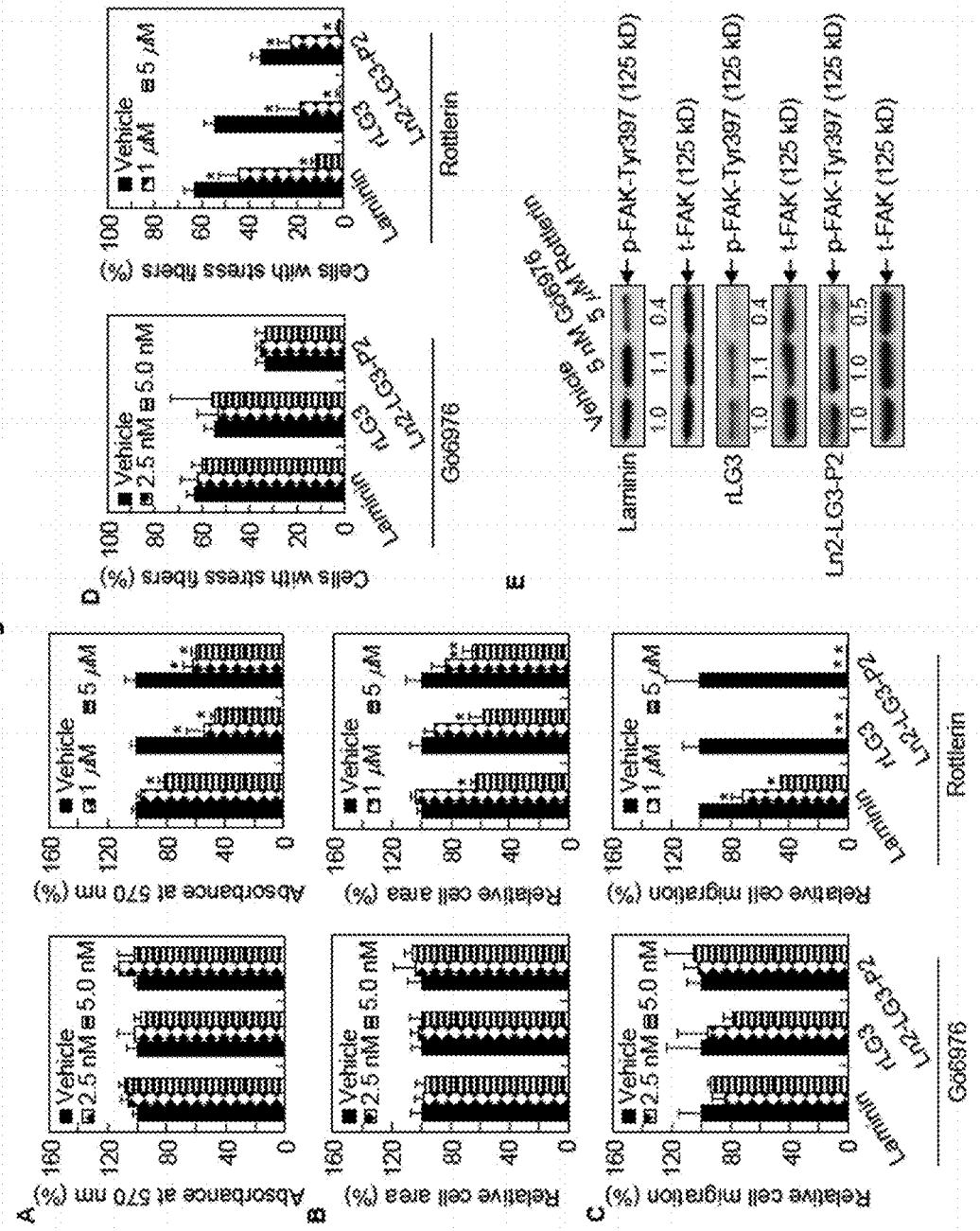

FIG. 8 is graphs and a diagram of roles of PKCα and PKCδ in cell adhesion, spreading, migration, stress fiber formation, and FAK phosphorylation at Tyr-397 induced by rLG3 and Ln2-LG3-P2-peptide according to the present invention:

FIGS. 8A to 8D are graphs showing cell adhesion (8A), spreading (8B), migration (8C), and stress fiber formation (8D) observed in PC12 cells which were pretreated with Gö6976 or rottlerin and cultured on laminin-, rLG3-, or Ln2-LG3-P2-coated dishes;

\*: p<0.01;

\*\*: p<0.05;

■: vehicle (dimethylsulfoxide, DMSO);

Go6976 treatment;

▨: the group pretreated with 2.5 nM Gö6976;

▤: the group pretreated with 5.0 nM Gö6976;

Rottlerin treatment;

▨: the group pretreated with 1 µM rottlerin;

▤: the group pretreated with 5 µM rottlerin; and

FIG. 8E is a diagram showing the extent of FAK phosphorylation observed in PC12 cells which were pretreated with Gö6976 or rottlerin for 15 min and cultured on laminin-, rLG3-, or Ln2-LG3-P2-coated dishes for 15 min at 37° C.

Figure 9:
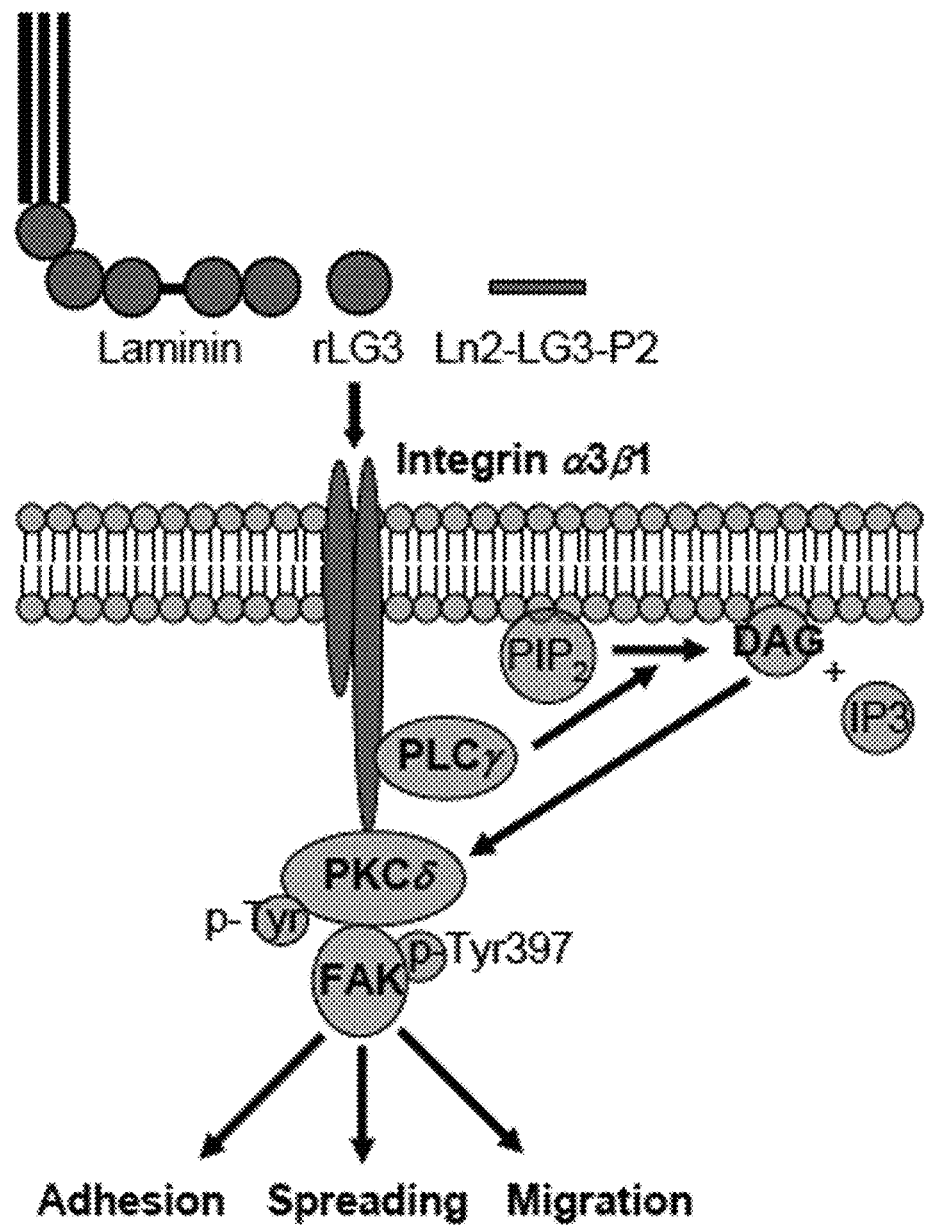

FIG. 9 is a diagram showing a mechanism for promotion of cell adhesion, spreading, migration, and neurite outgrowth by the binding of α3β1 integrin with laminin, Ln2-LG3-P2 peptide, and LG3 domain comprising the peptide within the human laminin α2 chain.

Figure 10:
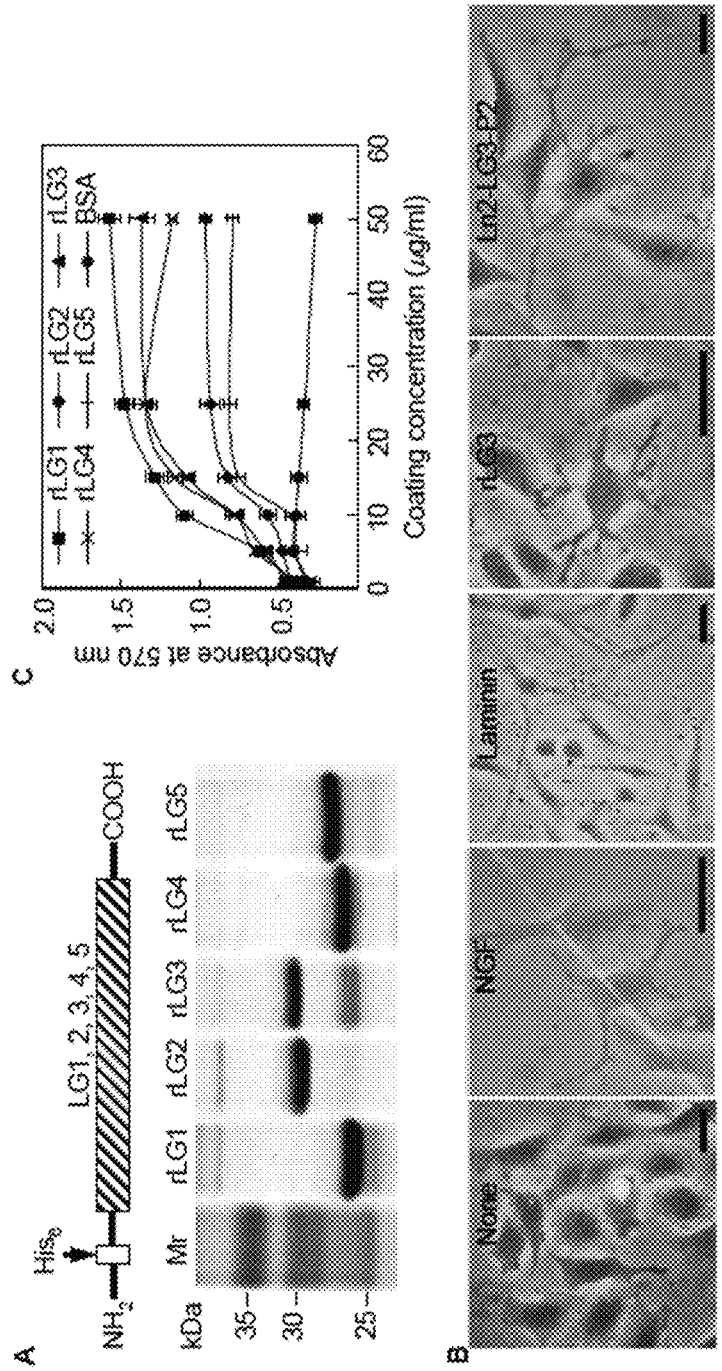

FIG. 10 is diagrams and a graph illustrating results of cellular activities of purified rLG domain proteins of human laminin α2 chain analyzed by SDS-PAGE and circular dichroism:

FIG. 10A illustrates a schematic diagram of five rLG domain proteins and a diagram identifying the expression of the $His_6$-tagged fusion rLG domain proteins with SDS-PAGE analysis;

FIG. 10B is a diagram showing neurite outgrowth of PC12 cells cultured on 12-well plates coated with laminin (5 µg/mL), rLG3 (25 µg/mL), or Ln2-LG2-P2 (62.5 µg/mL);

—: 25 µm;

FIG. 10C is a graph showing that rLG domain proteins increase adhesion of PC12 cells;

■: the group coated with rLG1(25 µg/mL);

♦: the group coated with rLG2(25 µg/mL);

▲: the group coated with rLG3(25 µg/mL);

x: the group coated with rLG4(25 µg/mL);

I: the group coated with rLG5(25 µg/mL); and

●: the group coated with BSA.

Figure 11:
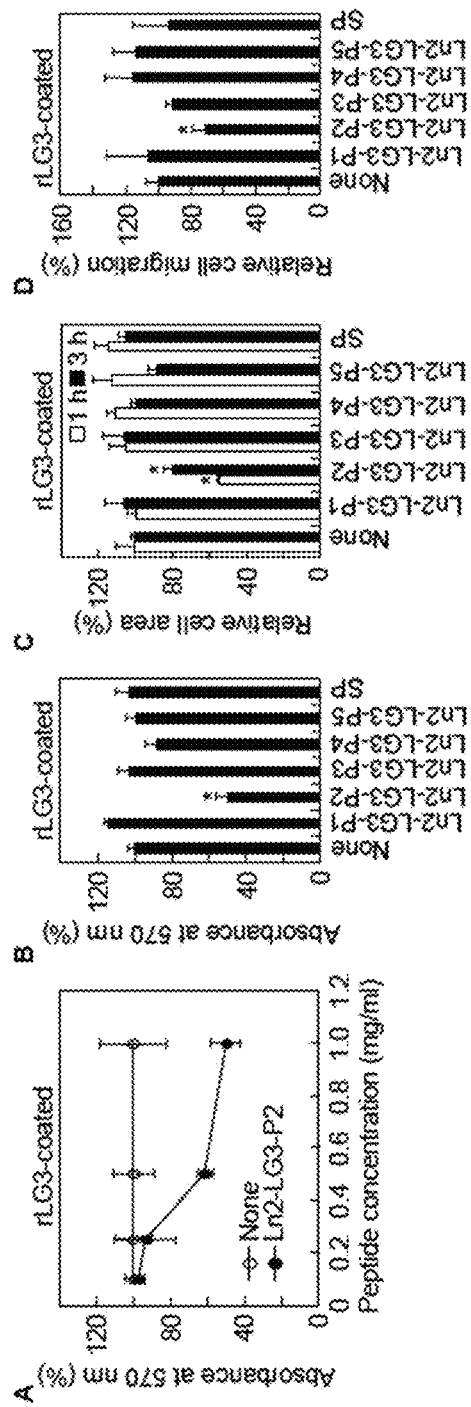

FIG. 11 is graphs showing inhibition of cell adhesion, spreading, migration, and neurite outgrowth promotion to rLG3 by Ln2-LG3-P2 peptide pretreatment:

FIG. 11A is a graph showing inhibition of cell adhesion in which PC12 cells were pretreated with 0 to 1.2 µg/mL of Ln2-LG3-P2 peptides and cultured on plates coated with rLG3 (25 µg/mL);

○: the group pretreated without Ln2-LG3-P2;

●: the group pretreated with Ln2-LG3-P2;

FIG. 11B is a graph showing inhibition of cell adhesion in which PC12 cells were pretreated with 500 µg/mL of Ln2-LG3-P2 peptide and cultured on plates coated with rLG3 (25 µg/mL);

\*: p<0.01;

FIG. 11C is a graph showing inhibition of cell spreading in which PC12 cells were pretreated with 500 µg/mL of Ln2-LG3-P2 peptide and cultured on plates coated with rLG3 (25 µg/mL) for 1 h or 3 h;

☐: the group cultured for 1 h;

■: the group cultured for 3 h;

\*: p<0.01;

FIG. 11D is a graph showing inhibition of cell migration in which PC12 cells were pretreated with 500 µg/mL of Ln2-LG3-P1, Ln2-LG3-P2, Ln2-LG3-P3, Ln2-LG3-P4, Ln2-LG3-P5 peptides and scramble peptide (SP, SEQ ID NO:20) and cultured in the upper chamber of transwell filters coated with rLG3 (25 µg/ml); and \*: p<0.01.

Figure 12:
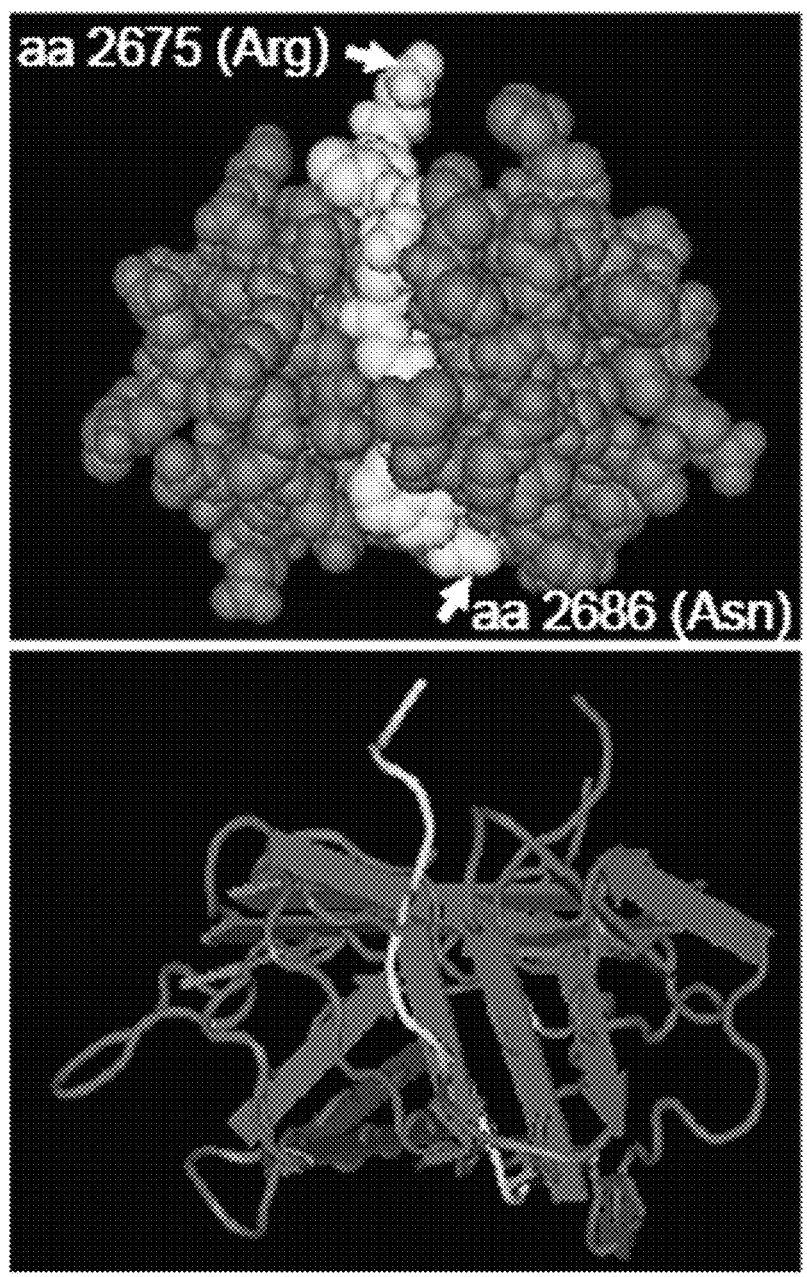

FIG. 12 shows the space-filling model (upper) and ribbon diagram (lower) illustrating Ln2-LG3-P2 positioned on the surface of the LG3 domain in the human laminin α2 chain.

Figure 13:
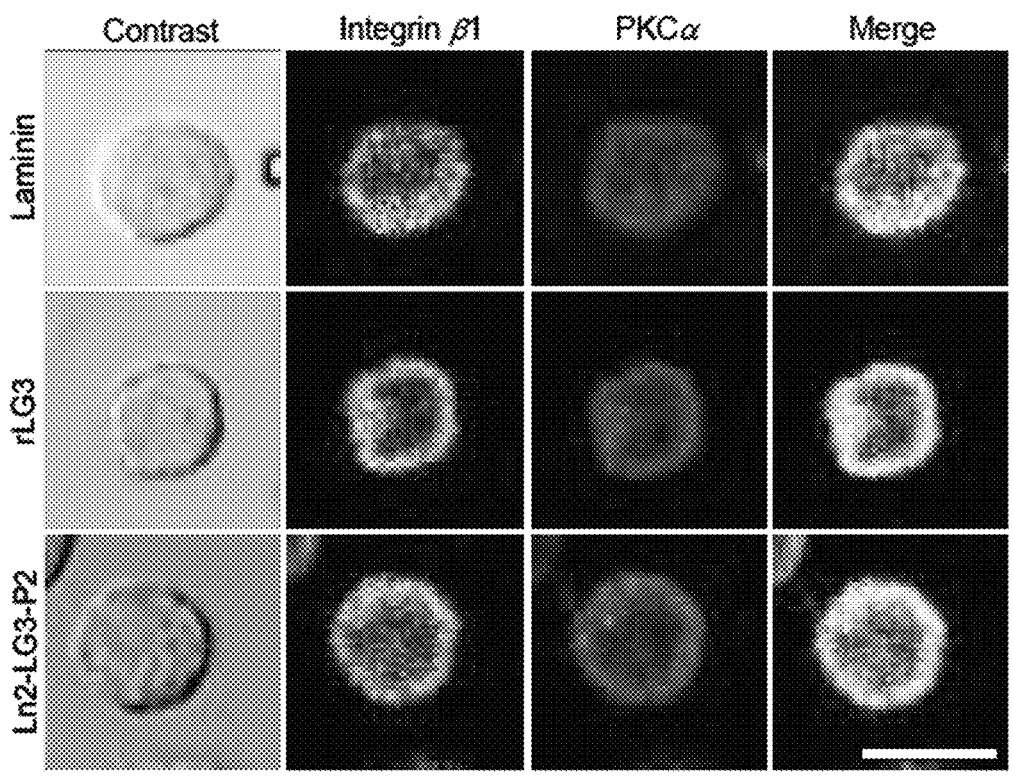

FIG. 13 is a diagram of colocalization of PKCα with integrin β1.

Figure 14:
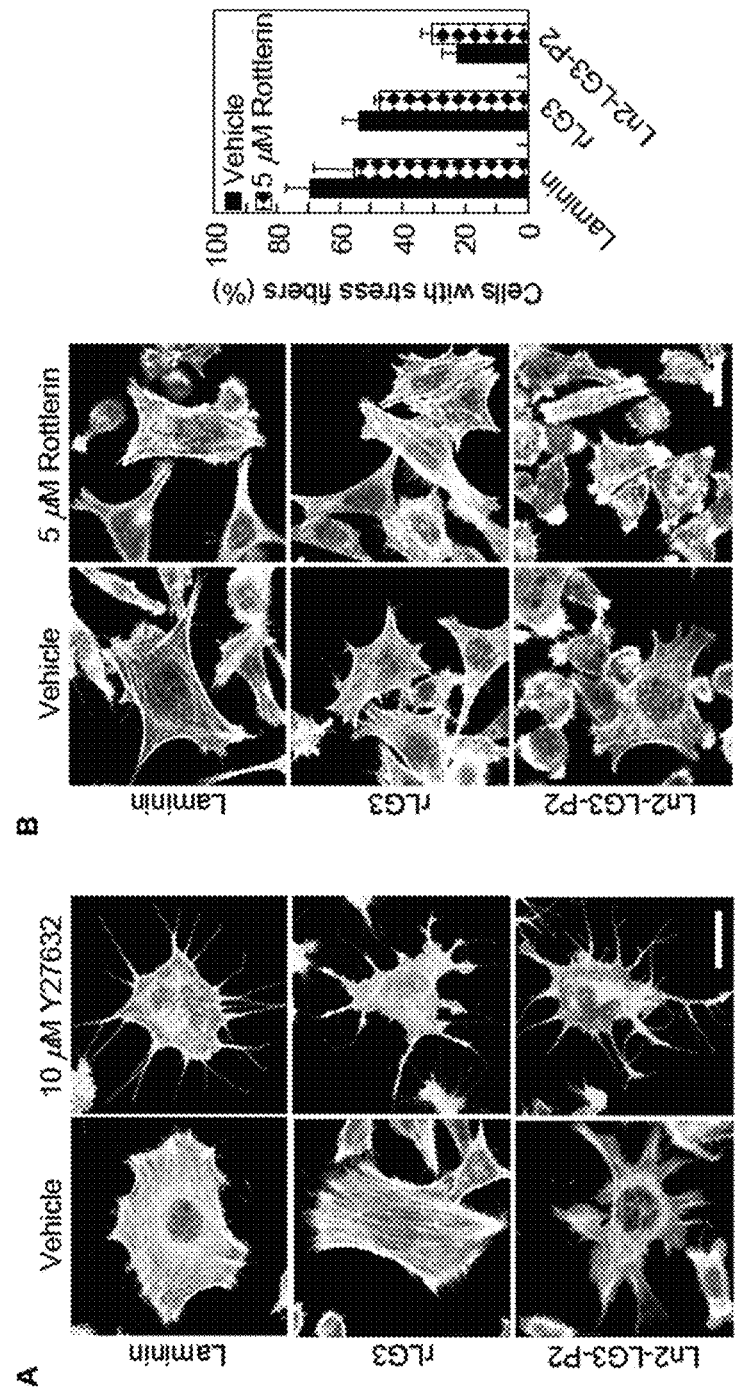

FIG. 14 is diagrams and a graph showing that stress fibers of PC12 cells to rLG3 and Ln2-LG3-P2 peptide are disassembled by an inhibitor of Rho-kinase, Y27632 treatment:

FIG. 14A is a diagram showing the result of immunostaining PC12 cells with rhodamine-phalloidin in which PC12 cells were cultured on glass slide chambers coated with rLG3 or Ln2-LG3-P2 for 1 h and treated with 10 µM Y27632 for 2 h;

FIG. 14B is a diagram showing the result of immunostaining PC12 cells with rhodamine-phalloidin in which PC12 cells were cultured on glass slide chambers coated with rLG3 or Ln2-LG3-P2 for 2.5 h and treated with 5 µM rottlerin for 30 min;

■: vehicle (dimethylsulfoxide, DMSO); and

▨: 5 µM rottlerin treatment.

Figure 15:
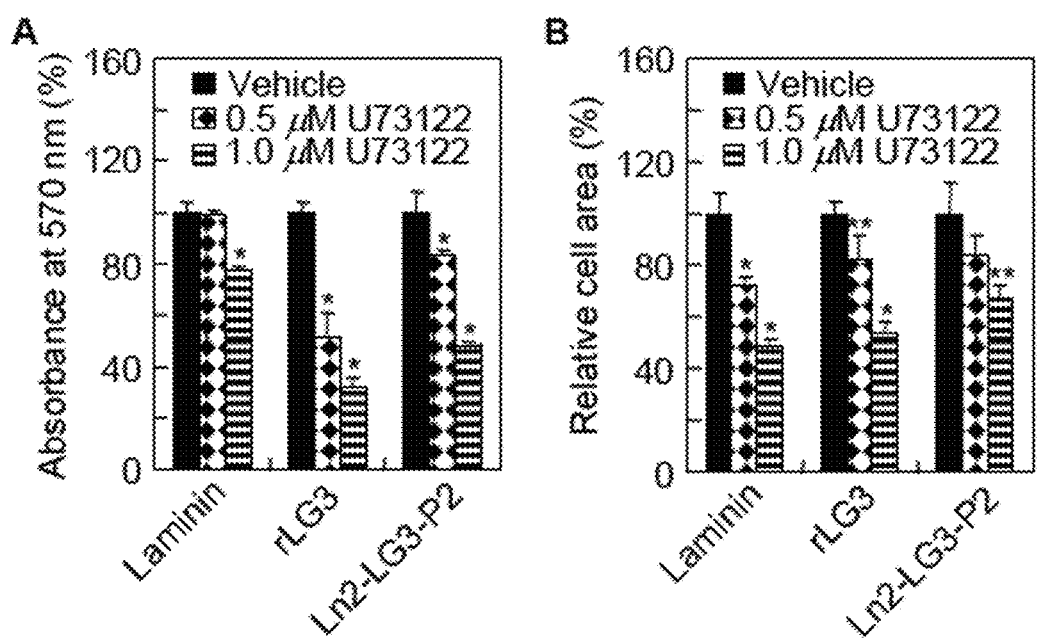

FIG. 15 is graphs showing that cell adhesion and spreading of PC12 cells to rLG3 and Ln2-LG3-P2 peptide are reduced by an inhibitor of phospholipase C (PLC), U73122 treatment:

FIG. 15A is a graph showing that cell adhesion is reduced by U73122 in a dose-dependent manner when PC12 cells pretreated with U73122 were cultured on plates coated with rLG3 and Ln2-LG3-P2 peptide for 1 h;

■: vehicle (dimethylsulfoxide, DMSO);

▨: 0.5 µM U73122 treatment;

▤: 1.0 µM U73122 treatment;

FIG. 15B is a graph showing that cell adhesion is reduced by U73122 in a dose-dependent manner when PC12 cells pretreated with U73122 were cultured on plates coated with rLG3 and Ln2-LG3-P2 peptide for 3 h;

■: vehicle (dimethylsulfoxide, DMSO);

▨: 0.5 µM U73122 treatment; and

▤: 1.0 µM U73122 treatment.

DESCRIPTION OF THE PREFERRED EMBODIMENTS

Hereinafter, the present invention will be described in detail.

The present invention provides a method of promoting cell adhesion, spreading, migration, growth, or regeneration in an individual, comprising administering a polypeptide or peptide to the individual, in which the polypeptide may include human laminin-2 α2 chain large globular (LG) 3 domain sequence, and the peptide may be an active peptide included in the human laminin-2 α2 chain large globular (LG) 3 domain sequence and consisting of one amino acid sequence selected from the group consisting of SEQ ID NOs: 1 and 35 to 50.

According to an embodiment, the human laminin-2 α2 chain large globular (LG) 3 domain sequence may consist of an amino acid sequence represented by SEQ ID NO: 2.

According to an embodiment, the polypeptide or the peptide may bind to α3β1 integrin.

According to an embodiment, the polypeptide or the peptide may regulate the intracellular location of protein kinase δ (PKCδ) through binding with α3β1 integrin.

According to an embodiment, the polypeptide or the peptide may induce tyrosine phosphorylation of PKCδ and focal adhesion kinase (FAK).

According to an embodiment, the tyrosine phosphorylation of focal adhesion kinase (FAK) may include tyrosine phosphorylation at Tyr-397 in FAK.

According to an embodiment, the polypeptide or the peptide may promote cell neurite growth.

According to an embodiment, the cell may be selected from the group consisting of PC12, CV-1, NIH/3T3, Scwann cells, normal human epidermal keratinocyes, normal human oral keratinocytes, and normal human dermal fibroblasts.

According to an embodiment, the polypeptide or the peptide may be used for treatment of burns or wounds.

According to an embodiment, the polypeptide or the peptide may be used for tissue regeneration.

The present invention provides a pharmacological composition for nerve regeneration comprising a polypeptide comprising human laminin-2 α2 chain large globular (LG) 3 domain sequence.

The human laminin-2 α2 chain LG3 domain sequence may have the amino acid sequence represented by SEQ ID NO:2, but is not limited to such.

The peptide may bind to α3 μl integrin, but is not limited to such. In addition, the polypeptide may regulate the intracellular location of protein kinase 5 (PKCδ) through binding with α3β1 integrin, but is not limited to such. In addition, the polypeptide may induce tyrosine phosphorylation of PKCδ and focal adhesion kinase (FAK) and the tyrosine phosphorylation of FAK may include tyrosine phosphorylation at Tyr-397 in FAK, but is not limited to such.

Figure 1:
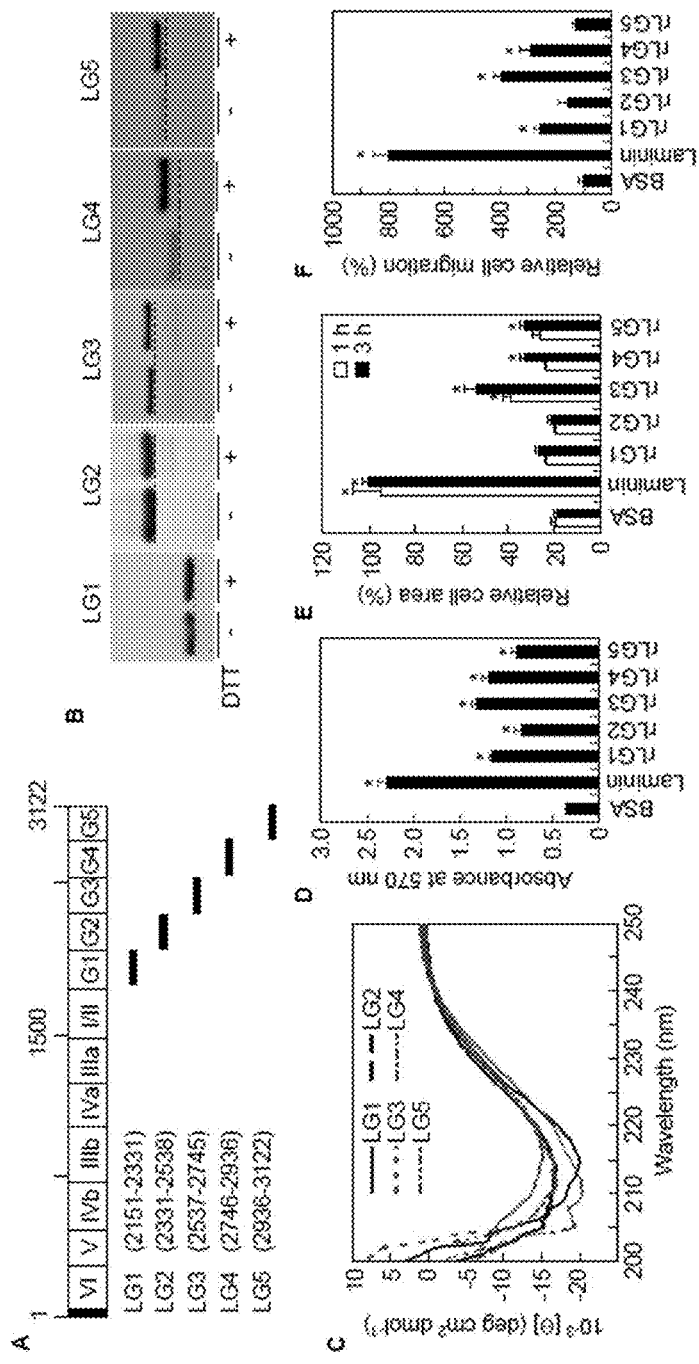
FIG. 1 is diagrams and graphs illustrating results of cellular activities of purified rLG domain proteins of human laminin α2 chain analyzed by SDS-PAGE and circular dichroism.

In detailed examples of the present invention, to identify a biologically active motif within the human laminin α2 chain involving in integrin-mediated cell adhesion, spreading, migration, and neurite outgrowth promotion, the present inventors cloned five kinds of domains in the human laminin α2 chain, expressed and obtained each domain protein (FIG. 10). Then, the present inventors characterized the structures and biological activities of the obtained LG1 to LG5 domain proteins and by culturing nerve cells on plates coated with rLG domain proteins, the present inventors found out that among rLG domain proteins, rLG3 domain protein can promote cell adhesion, spreading, migration, and neurite outgrowth of nerve cells best (FIG. 1 and FIG. 10).

In detailed examples of the present invention, the present inventors synthesized amino acid fragments constituting LG3 domain which showed the highest biological activities and identified an authentic motif showing the activities. When plates were coated with Ln2-LG3-P2 sequence having the amino acid sequence represented by SEQ ID NO:1 and then cells were cultured on the plates, cell adhesion, spreading, migration, and neurite outgrowth occurred the most actively and these were observed also in various nerve cells (FIG. 2).

In detailed examples of the present invention, the major residue and sequence involving in promoting cell adhesion, spreading, migration, and neurite outgrowth were identified using mutant rLG3 of amino acid residue Arg in the Ln2-LG3-P2 peptide of the present invention substituted to Ala and N- or C-terminal truncated peptides or added sequences of the Ln2-LG3-P2 peptide (FIG. 3 and FIG. 5). In addition, as a result of evaluating a detailed mechanism of this cell adhesion, FAK phosphorylation was observed due to the interaction between α3β1 integrin and Ln2-LG3-P2 peptide when integrin-mediated cell adhesion to Ln2-LG3-P2 protein occurred and it was observed specifically at Tyr-397 (FIG. 6). Furthermore, the inventors found out that PKCα and PKCδ isoforms are translocated to integrin and the activation of PKCδ is essential for cell adhesion (FIG. 7 and FIG. 8).

That is, the LG3 domain represented by SEQ ID NO:2 in human laminin-2 α2 chain according to the present invention can support cell adhesion, spreading, migration, and neurite outgrowth of nerve cells better than other domains and thus, a composition comprising the LG3 domain as an active ingredient can be used for a pharmaceutical composition for nerve regeneration.

The composition of the present invention may be administered orally or parenterally (for example, topical application, intravenous injection, subcutaneous injection, and intra-abdominal injection) and oral administration is preferable.

Preparations for parenteral administration may be formulated as powders, granules, tablets, capsules, sterile solutions, liquid, water-insoluble excipients, suspensions, emulsions, syrups, suppositories, external preparations such as aerosols, etc., and sterile injections by general methods and preferably, skin external pharmaceutical compositions such as creams, gels, patches, sprays, ointments, plasters, lotions, liniments, pastes, and cataplasma may be prepared to use, but not limited to such. Compositions for local administration may be formulated as an anhydrous type or a hydrous type according to clinical prescription. Propylene glycol, polyethylene glycol, vegetable oil such as olive oil, and injectable ester such as ethylolate, etc. may be used for water insoluble excipients and suspensions. Witepsol, macrogol, tween 61, cacao butter, laurin butter, glycerogelatin, etc. may be used for a suppository base.

Solid formulations for oral administration include powders, granules, tablets, capsules, soft capsules, pills, etc. Liquid formulation for oral administrations include suspensions, liquid for internal use, emulsions, syrups, aerosols, etc. and various excipients such as wetting agents, sweeteners, aromatics, preservatives, etc. in addition to generally-used simple diluents such as water and liquid paraffin may be included.

For administration, the compositions may further comprise one or more pharmaceutically acceptable carriers in addition to the polypeptide comprising human laminin-2 α2 chain LG3 domain sequence. Saline, sterilized water, Ringer's solution, buffered saline, dextrose solution, maltodextrin solution, glycerol, ethanol, and a mixture comprising one or more of those components may be used for the pharmaceutically acceptable carrier and general additives such as antioxidants, buffers, bacteriostatic agents, etc. may be added, if necessary. The composition may be formulated as preparations for injection such as aqueous solutions, suspensions, emulsions, etc. by mixing with diluents, dispersing agents, surfactants, binders and lubricants.

The pharmaceutically acceptable additive according to the present invention may be included in the composition in an amount of from about 0.1 to about 90 parts by weight with respect to the composition, but not limited to such.

The preferred administration dose of the composition of the present invention may be different depending on degrees of absorption in human bodies, age, gender, and severity of obesity of patient and be selected appropriately by the person skilled in the art. For preferable effects, in a case for preparation for oral administration, the composition of the present invention may be administered generally for adults in a dose of from about 0.0001 to about 100 g/kg body weight per day, preferably from about 0.001 to about 100 mg/kg. The administration frequency may be once a day or a few times a day.

The administration dose is not intended to limit the scope of the present invention in any way.

The pharmaceutical composition for nerve regeneration of the present invention may further comprise one or more active ingredients having the same or similar function in addition to the peptide comprising human laminin-2 α2 chain LG3 domain sequence.

The present invention also provides a pharmacological composition for nerve regeneration comprising a peptide having the amino acid sequence represented by SEQ ID NO:1, as an active peptide in human laminin-2 α2 chain LG3 domain sequence.

The active peptide in human laminin-2 α2 chain LG3 domain sequence may have the amino acid sequence represented by SEQ ID NO:1, but not limited to such, and may be located in human laminin-2 α2 chain LG3 domain represented by SEQ ID NO:2. In addition, the peptide may bind to α3β1 integrin, but is not limited to such. In addition, the polypeptide may regulate the intracellular location of PKCδ through binding with α3β1 integrin, but is not limited to such. In addition, the polypeptide may induce tyrosine phosphorylation of PKCδ and FAK and the tyrosine phosphorylation of FAK may include tyrosine phosphorylation at Tyr-397 in FAK, but is not limited to such. In addition, the nerve cell may be selected from the group consisting of PC12, CV-1, NIH/3T3, Schwann cells, normal human epidermal keratinocytes, normal human oral keratinocytes, and normal human dermal fibroblasts, but is not limited to such.

That is, the present inventors found out that the Ln2-LG3-P2 peptide represented by SEQ ID NO:1 and the LG3 domain protein comprising thereof according to the present invention show the integrin-mediated cell adhesion, spreading, migration, and neurite outgrowth promotive effects and these are achieved through the translocation of PKCα and PKCδ, PKC isoforms to the integrin and tyrosine phosphorylation at Tyr-397 of FAT and phosphorylation of PKCδ and thus, the peptide represented by SEQ ID NO:1 according to the present invention can be used for the active ingredient of the pharmaceutical composition for nerve regeneration.

Furthermore, the present invention provides a pharmacological composition for nerve regeneration comprising a peptide having one amino acid sequence selected from the group consisting of amino acid sequences represented by SEQ ID NOs:35 to 50, as an active peptide in human laminin-2 α2 chain LG3 domain sequence.

The peptide having one amino acid sequence selected from the group consisting of amino acid sequences represented by SEQ ID NOs:35 to 50 may present in the human laminin-2 α2 chain LG3 domain sequence represented by SEQ ID NO:2, preferably in the active peptide represented by SEQ ID NO:1, but not limited to such.

In addition, the pharmaceutical composition for nerve regeneration may comprise the peptide having one amino acid sequence selected from the group consisting of SEQ ID NOs:37, 49, and 50, but not limited to such. Since the peptides represented by SEQ ID NOs:35 to 50 have excellent effects on promoting cell adhesion, spreading, migration, and neurite outgrowth, a composition comprising one peptide selected from those peptides can be used for the pharmaceutical composition for nerve regeneration.

In addition, the peptide may bind to α3 μl integrin, but is not limited to such. In addition, the polypeptide may regulate the intracellular location of PKCδ through binding with α3β1 integrin, but is not limited to such. In addition, the polypeptide may induce tyrosine phosphorylation of PKCδ and FAK and the tyrosine phosphorylation of FAK may include tyrosine phosphorylation at Tyr-397 in FAK, but is not limited to such. In addition, the nerve cell may be selected from the group consisting of PC12, CV-1, NIH/3T3, Schwann cells, normal human epidermal keratinocytes, normal human oral keratinocytes, and normal human dermal fibroblasts, but is not limited to such.

In detailed examples of the present invention, to determine the biologically active core sequence in the active peptide present in the human laminin-2 α2 chain LG3 domain sequence represented by SEQ ID No: 1, sixteen peptides that are N- or C-terminal truncated peptides, or C-terminal added peptides of the Ln2-LG3-P2 were synthesized (Table 1. and FIG. 5) and examined for biological activities thereof. The cell adhesion, spreading, migration, and neurite outgrowth promotive effects of the peptides having amino acid sequences represented by SEQ ID NOs:35 to 50 were similar or more excellent than those of rLG3 domain. Especially, the activities of the peptides having amino acid sequences represented by SEQ ID NOs:37, 49, and 50 were significantly excellent.

Since amino acid sequences represented by SEQ ID NOs: 35 to 50 are core sequences among the active peptides in human laminin-2 α2 chain LG3 domain sequence and have effects on promoting cell adhesion, spreading, migration, and neurite outgrowth, the composition comprising them can be used for regeneration of nerve cells.

The present invention also provides an agent for promoting adhesion, spreading, migration, and neurite outgrowth of nerve cells comprising the human laminin-2 α2 chain LG3 domain or the active peptide in the domain according to the present invention.

The human laminin-2 α2 chain LG3 domain of the present invention may have the amino acid sequence represented by SEQ ID NO:2 and the active peptide in the domain may have one amino acid sequence selected from the group of SEQ ID NOs:1 and 35 to 50.

In detailed examples of the present invention, among five domains in the human laminin-2 α2 chain, LG3 domain showed the promotive effect on cell adhesion, spreading, migration, and neurite outgrowth of nerve cells and in the LG3 domain, the highest biological activities were observed in the peptide having the amino acid sequence represented by SEQ ID NO:1. As a result of examining the biological activities using peptides that are N- or C-terminal truncated peptides, or C-terminal added peptides of the active peptide represented by SEQ ID NO:1, the promotive effects on cell adhesion, spreading, migration, and neurite outgrowth of the peptides having amino acid sequences represented by SEQ ID NOs:35 to 50 were excellent.

Thus, the human laminin-2 α2 chain LG3 domain or the active peptide in the domain according to the present invention can be used as an agent for promoting adhesion, spreading, migration, and neurite outgrowth of nerve cells.

The active ingredient of the agent for promoting adhesion, spreading, migration, and neurite outgrowth of nerve cells of the present invention may be administered parenterally when clinically administered, and used in the form of general pharmaceutical preparations. That is, the agent for promoting adhesion, spreading, migration, and neurite outgrowth of nerve cells of the present invention can actually be administered by various parenteral formulations. Generally used diluents, such as fillers, extenders, binders, wetting agents, disintegrants and surfactants, or excipients are used for pharmaceutical preparations. The pharmaceutical preparation for parenteral administration includes sterilized aqueous solution, water-insoluble excipients, suspensions, emulsifiers, and freeze-dried preparations. Propylene glycol, polyethylene glycol, vegetable oil such as olive oil, ethylolate, etc. may be used for water-insoluble excipients and suspensions.

The agent for promoting adhesion, spreading, migration, and neurite outgrowth of nerve cells may be mixed for use with pharmaceutically acceptable carriers such as physiological saline or organic solvents. To increase stability or absorption of the agent promoting cell adhesion, carbohydrates such as glucose, sucrose, or dextran, antioxidants such as ascorbic acid or glutathione, chelating agents, low molecular proteins or other stabilizers may be used as drugs.

Total effective dose of the agent for promoting adhesion, spreading, migration, and neurite outgrowth of nerve cells of the present invention may be administered to patients with single dose in the form of bolus or by infusion for a relatively short period, and may also be administered with multiple doses for a long period of time by fractionated treatment protocol. Since the concentration of the agent for promoting adhesion, spreading, migration, and neurite outgrowth of nerve cells is determined by consideration of various factors such as pharmaceutical administration pathway, treatment frequency as well as age and health condition of patient, the person skilled in the art would be able to determine an appropriate effective dose according to specific use as the pharmaceutical composition of the agent for promoting adhesion, spreading, migration, and neurite outgrowth of nerve cells.

Furthermore, the present invention provides a container for promoting nerve cell adhesion, spreading, migration, and neurite outgrowth comprising the human laminin-2 α2 chain LG3 domain or the active peptide in the domain.

The nerve cell may be selected from the group consisting of PC12, CV-1, NIH/3T3, Schwann cells, normal human epidermal keratinocytes, normal human oral keratinocytes, and normal human dermal fibroblasts, but is not limited to such.

The container for promoting nerve cell adhesion, spreading, migration, and neurite outgrowth may be one selected from cell culture dishes, petri dishes, tissue culture flasks, plates, vessels, slides, filter chambers, slide chambers, roller bottles, harvesters, and tubes, but is not limited to such.

The present invention also provides a method of promoting nerve cell adhesion, spreading, migration, and neurite outgrowth, the method comprising:

(1) fixing the human laminin-2 α2 chain LG3 domain or the active peptide in the domain according to the present invention to a solid support; and (2) promoting nerve cell adhesion, spreading, migration, and neurite outgrowth at the solid support.

The nerve cell may be selected from the group consisting of PC12, CV-1, NIH/3T3, Schwann cells, normal human epidermal keratinocytes, normal human oral keratinocytes, and normal human dermal fibroblasts, but is not limited to such.

In detailed examples of the present invention, since the human laminin-2 α2 chain LG3 domain (SEQ ID NO:2) or the active peptides in the domain (SEQ ID NOs:1, 35 to 50) have the promotive effects on adhesion, spreading, migration, and neurite outgrowth of nerve cells, these can be used for promoting adhesion, spreading, migration, and neurite outgrowth of nerve cells.

Furthermore, the present invention provides a therapeutic agent for burns or wounds comprising the human laminin-2 α2 chain LG3 domain or the active peptide in the domain.

Since the polypeptide represented by SEQ ID NO:2, peptides having amino acid sequences represented by SEQ ID NOs:1, 35 to 50 of the present invention promote cell adhesion, spreading, migration, and neurite outgrowth, these can be used for burns or wounds treatment.

The present invention also provides an artificial nerve conduit or its scaffolds comprising the human laminin-2 α2 chain LG3 domain or the active peptide in the domain.

The polypeptide represented by SEQ ID NO:2, peptides having amino acid sequences represented by SEQ ID NOs:1, 35 to 50 of the present invention promote cell adhesion, spreading, migration, and neurite outgrowth. Accordingly, when the polypeptide, peptides, or derivatives thereof are used for producing an artificial nerve conduit by coating, attaching, or chemical bonding, they can promote adhesion of nerve cells. Thus, when the artificial nerve conduit is injected into living bodies, it can regenerate nerve cells.

Furthermore, the present invention provides a scaffold for tissue engineering comprising the human laminin-2 α2 chain LG3 domain or the active peptide in the domain.

Scaffolds for tissue engineering according to the present invention include all scaffolds which can be used in tissue engineering field for maintenance, improvement, or restoration of body functions by transplantation of a substitute for living body tissue. These scaffolds for tissue engineering include porous scaffolds prepared with synthetic biodegradable polymer compounds such as poly amino acid, poly anhydride, poly ε-caprolactone, polyorthoester, polyglycollic acid (PGA), polylactic acid (PLA), copolymers thereof such as polylactic-polyglycollic acid (PLGA), and natural biodegradable polymer compound such as alginic acid, chitosan, hyaluronic acid, and collagen. The scaffolds for tissue engineering may include shields and porous polylactic acid shield, a regeneration membrane made of chitin or chitosan nanofiber, or film-shaped shield made of chitin or chitosan may be used for the shields, but are not limited thereto.

Hereinafter, the present invention will be described in more detail with reference to the following examples and experimental examples.

However, the following examples and experimental examples are provided for illustrative purposes only, and the scope of the present invention should not be limited thereto in any manner.

Example 1

Cell Culture

<1-1> PC12 Cell Culture

The PC12 cell line (CRT-1721™, ATCC) from transplantable rat pheochromocytoma was cultured in RPMI 1640 medium (BioWhittaker Cambrex, Walkersville, Md.) containing antibiotics and 10% fetal bovine serum (FBS) at 37° C. with a 5% $CO_2$ humid atmosphere.

<1-2> NIH/3T3 Cell Culture

The mouse embryo fibroblast cell line NIH/3T3 was purchased from the American Type Culture Collection (Manassas, Va.) and cultured in Dulbecco's modified Eagle's medium (DMEM) containing 10% FBS.

<1-3> CV-1 Cell Culture

The normal African green monkey kidney fibroblast cell line CV-1 was purchased from the American Type Culture Collection (Manassas, Va.) and cultured in DMEM containing 10% FBS.

<1-4> Schwann Cell Culture

Schwann cells, nerve cells used in the present invention, were obtained from human skin-derived precursors by differentiating the cells toward the Schwann cell lineage for two weeks and identified by immunocytochemical markers specific to Schwann cells, such as S100D and glial fibrillary acidic protein (GFAP) (Biernaskie, J. A. et al., *Nat. Protoc.*, 2006).

<1-5> Normal Human Epidermal Keratinocyte Culture

Normal human epidermal keratinocytes (NHEK) isolated from epidermal tissue of normal human epidermal skin were cultured in keratinocyte growth medium (KGM, manufactured by Clonetics, San Diego, Calif.). Cells at passage 2 were used for the following experiments.

<1-6> Normal Human Oral Keratinocyte Culture

Normal human oral keratinocytes (NHOK) isolated from epidermal tissue of human gingiva were cultured in KGM (by Clonetics, San Diego, Calif.). Cells at passage 2 were used for the following experiments.

<1-7> Normal Human Dermal Fibroblast Culture

Normal human dermal fibroblasts (NHDF) isolated from hypodermal tissue of normal human skin were cultured in DMEM containing antibiotics and 10% FBS. Cells at passage 4 were used for the following experiments.

Example 2

Preparation of Vector for Expression of Human Laminin α2 Chain LG Domain

The present inventors disclosed that three human laminin α2 C-terminal LG domains, LG1 to LG3 domains promote cell adhesion activity in the previous study. Although LG1 domain having a biological active sequence disclosed in the previous study induce cell adhesion, it does not perform the other functions such as cell spreading, migration, and neurite outgrowth (Jung, S. Y, et al., *J. Biol. Chem.*, 2009).

To identify functional domain within the human laminin α2 chain and to clarify biologically active sequences conferring various functional activities in human laminin α2 chain, five human laminin α2 C-terminal LG domains (LG1 to LG5) were individually cloned by reverse transcriptase-polymerase chain reaction (RT-PCR) from human keratinocytes and fibroblasts, and each LG domain was separately expressed in *E. coli*.

<2-1> Human Laminin α2 Chain LG Domain Cloning

To identify biologically active sequences of LG1 to LG5, five human laminin α2 C-terminal LG domains, the present inventors performed RT-PCR using the human laminin α2 chain cDNA.

Specifically, the human laminin α2 chain cDNA was cloned using a RT-PCR with Superscript II Reverse Transcriptase (Invitrogen, Carlsbad, Calif.) according to the manufacturer's instructions by using mRNA isolated from human keratinocytes and fibroblasts. Five LG domains cDNA fragments (LG1-LG5) of the laminin α2 chain C-terminal LG domain were amplified by PCR using the laminin α2 chain cDNA as a template and ligated into the pGEM-T Easy vector (Promega, Madison, Wis.). The PCR primers used were as follows:

```
LG1-1 sense primer:
                                    (SEQ ID NO: 3)
5'-AAACAAGCCAATTCTATCAA-3';

LG1-1 antisense primer:
                                    (SEQ ID NO: 4)
5'-ATTTCCATTTCCCATCATT-3';

LG1 sense primer:
                                    (SEQ ID NO: 5)
5'-GCCACTCGAGCAGGAGGTGACTG-3';

LG1 antisense primer:
                                    (SEQ ID NO: 6)
5'-GCCACCATGGTCAACTGACAGTGCATCC-3';

LG2 sense primer:
                                    (SEQ ID NO: 7)
5'-GCCACTCGAGCAGTCCTCAGGTG-3';

LG2 antisense primer:
                                    (SEQ ID NO: 8)
5'-GCCACCATGGTCACTCCACAAAACCAGGCTTA-3';

LG3 sense primer:
                                    (SEQ ID NO: 9)
5'-GCCACTCGAGTGTGGAGCTCTCCCCTGT-3';

LG3 antisense primer:
                                    (SEQ ID NO: 10)
5'-GCCACCATGGTCAAACTGGGGTGGGCGTAGGA-3';

LG4 sense primer:
                                    (SEQ ID NO: 11)
5'-GCCACTCGAGTCTGACACATGGTCCTTGTG-3';

LG4 antisense primer:
                                    (SEQ ID NO: 12)
5'-GCCACCATGGTCATGCAAAACATGTCCCAA-3';

LG5 sense primer:
                                    (SEQ ID NO: 13)
5'-GCCACTCGAGTGCAAATGCTCAGAGGGGA-3';
and LG5 antisense primer:
                                    (SEQ ID NO: 14)
5'-GCCACCATGGTCACCTGGGGTTACACTTATTTTTATT-3'.
```

LG1 was amplified by a nested PCR using two primer combinations: first with the LG1-1 sense and antisense primers, and then the product was amplified with the LG1 sense and antisense primers. Nucleotide sequences of all of the plasmid constructs were confirmed by sequence analysis. These cDNA fragments were digested with Xho I and Nco I, and inserted into corresponding sites of the mammalian expression plasmid vector pRSET (Invitrogen). Correct orientation of the inserts was verified by sequence analysis.

<2-2> Expression and Purification of Human Laminin α2 Chain LG Domain

Recombinant LG (rLG) were expressed and purified using the vector for expression of human laminin α2 chain LG domain cloned in Example <2-1>.

The expression and purification of rLG domain proteins were reported previously (Kim, J. M. et. al., *Exp. Cell Res.*, 2005). Specifically, the expression of rLG proteins were induced in *Escherichia coli* strain BL21 at MIDlog phase in Luria-Bertani medium using 1 mM isopropyl-β-D-thiogalactopyranoside (IPTG, manufactured by Promega). After induction of protein expression for 5 h at 37° C., the cells were harvested by centrifugation at 6000 rpm for 10 min. Cell pellets were kept at −80° C. until use.

To purify proteins, the cell pellets were dissolved in lysis buffer (100 mM $NaH_2PO_4$, 10 mM Tris-HCl, 8 M urea, pH 8.0) containing 1 mM phenylmethylsulfonyl fluoride (Sigma) and suspended. rLG domain proteins were purified using $Ni^{2+}$-nitrilotriacetic acid agarose (Qiagen, Valencia, Calif.). Purified recombinant histidine 6-tagged LG proteins were dialyzed sequentially from high to low concentrations (3 M, 2 M, 1 M, or 0.5 M) of urea in 10 mM Tris-HCl (pH 3.0) buffer containing 100 mM $NaH_2PO_4$ and 1 mM phenylmethylsulfonyl fluoride. Finally, these proteins were dialyzed against phosphate-buffered saline (PBS; pH 3.0) containing 1 mM phenylmethylsulfonyl fluoride.

The dialyzed rLG domain proteins were concentrated to 0.5 μg/μL using a Centricon equipment (Centricon YM-10, Millipore, Bedford, Mass.) and kept at −80° C. until use. The protein concentrations were determined using a Bio-Rad protein assay kit (BioRad, Hercules, Calif.).

The corresponding amino acid positions of the rLG domain proteins in the entire human laminin α2 chain LG are shown in FIG. 1A. Specifically, LG1 has amino acid sequence at position 2151 to 2331, LG2 has amino acid sequence at position 2331 to 2538, LG3 has amino acid sequence at position 2537 to 2745, LG4 has amino acid sequence at position 2746 to 2936, and LG5 has amino acid sequence at position 2936 to 3122 in the entire human laminin α2 chain LG (FIG. 1A). The molecular masses of the expected rLG1, rLG2, rLG3, rLG4, and rLG5 proteins were 24, 27, 27, 25, and 25 kDa, respectively, and as a result of purifying rLG proteins which were expressed in the BL21, each purified rLG domain protein showed the predicted molecular mass as shown in FIG. 10.

Experimental Example 1

Structure Analysis of Purified rLG Domain Proteins

<1-1> Determination of Disulfide Bond of rLG Domain Proteins

To determine whether or not an intramolecular disulfide bond is formed in the purified rLG proteins, the present inventors subjected the purified recombinant proteins to SDS-PAGE under reducing or nonreducing conditions and looked for mobility differences.

After 100 mM dithiothreitol (DTT) was treated to rLG domain proteins, 10% SDS-PAGE was performed. Gel mobilities of rLG domain proteins treated with DTT were compared to those of proteins without DTT treatment.

As shown in FIG. 1B, treatment of rLG domain proteins with 100 mM dithiothreitol (DTT) prior to SDS-PAGE caused a small but reproducible reduction in gel mobility, suggesting that intramolecular disulfide bonds are present in all five recombinant proteins (FIG. 1B).

<1-2> Structure Analysis of rLG Domain Proteins Using Circular Dichroism Spectroscopy To assess whether the bacterially expressed LG domain proteins are well folded, the secondary structure of rLG domain proteins was assessed by circular dichroism spectroscopy (CD Spectroscopy).

rLG domain proteins at 0.2 mg/mL were prepared in PBS. CD spectra were recorded on a Jasco spectropolarimeter (model J-715; Jasco International Co., Japan). Protein samples were analyzed at 23° C. from 180 to 300 nm with a 2 mm path length cell. Three repetitive scans were averaged and smoothed by binomial curve smoothing. The molar ellipticity (in degrees cm$^2$ dmol$^{-1}$) was calculated on the basis of protein concentration and molar mass for each rLG domain protein.

As shown in FIG. 1C, CD spectra of recombinant histidine 6 (His$_6$)-LG1, -LG2, -LG3, -LG4, and -LG5 showed ellipticity minima at 215, 212, 211, 210, and 216 nm, respectively (FIG. 1C). These results suggest that the bacterially expressed LG domains from human laminin α2 chain are sufficiently well folded to support potential cellular functions.

Experimental Example 2

Characterization of Biological Activities of rLG Domain Proteins

Because laminin α2 chain LG domains are known to have several active sites for cell adhesion, heparin binding, and neurite outgrowth, the present inventors examined for cellular activity to identify the cell binding domains.

<2-1> Measurement of Biological Activities of rLG Domain Proteins Through Cell Adhesion Assay The cell adhesion assay was performed as described in a paper published previously by the present inventors (Kim, J. M., et al, *Exp. Cell Res*, 2005).

Specifically, 24-well culture plates (Nunc, Denmark) were coated with 5 μg/mL human placental laminin (Sigma-Aldrich, St. Louis, Mo.) or 25 μg/mL rLG domain proteins for 12 h at 4° C. The peptides were also coated on the plates by drying for 12 h at room temperature. The substrate-coated plates were blocked with 1% heat-inactivated bovine serum albumin (BSA) in PBS for 1 h at 37° C. and then washed with PBS.

The cells were trypsinized with trypsin/EDTA and resuspended in serum-free culture medium. The cells were added at a density of $2 \times 10^5$ cells/500 μL to each plate and incubated in serum-free culture medium for 1 h at 37° C. After incubation, unattached cells were removed by rinsing twice with PBS. The attached cells were fixed with 10% formalin for 15 min and then stained with 0.5% crystal violet for 1 h. Plates were gently washed with distilled water three times and dissolved with 2% SDS for 5 min. Absorbance was measured at 570 nm using a microplate reader (BioRad).

As a result, it was observed that human placental laminin promoted cell adhesion in FIG. 1D. Although the levels of cell adhesion to rLG domain proteins were lower than that of laminin, PC12 cells adhered to rLG1, rLG3, and rLG4 in a dose-dependent manner but weakly attached to rLG2 and rLG5.

As shown in FIG. 10C, when PC12 cells were incubated on plates coated with rLG domain proteins in various concentrations of from 0 to 60 μg/mL for 1 h in serum-free medium, cell adhesion activity of the rLG domain proteins reached the maximum level at 25 μg/mL in PC12 cells (FIG. 10C).

<2-2> Measurement of Biological Activities of rLG Domain Proteins Through Cell Spreading Assay To determine cell spreading assays, the cells cultured on plates coated with each rLG domain protein for 1 h or 3 h in Experimental example <2-1> were fixed with 10% formalin. Then, the fixed cells were stained with 0.05% crystal violet for 1 h and plates were gently washed with PBS three times. The surface area of cells was measured with Image-Pro plus software (Version 4.5; Media Cybernetics, Silver Spring, Md.).

As shown in FIG. 1E, human placental laminin promoted cell spreading (FIG. 1E). rLG3, rLG4, and rLG5 induced cell spreading compared with BSA control, respectively, whereas rLG1 and rLG2 had no effect on cell spreading <2-3> Measurement of Biological Activities of rLG Domain Proteins Through Cell Migration Assay Cell migration assays were performed using transwell migration chambers of 8 μm in pore size (Corning Inc., NY) as described in a paper published previously by the present inventors (Kim, J. M., Min, S. K., Kim, H., Kang, H. K., Jung, S. Y., Lee, S. H., Choi, Y., Roh, S., Jeong, D., and Min, B. M. (2007) *Int. J. Mol. Med.*).

The lower sides of transwell filters were coated with laminin (5 μg/mL) or rLG proteins (25 μg/mL) for 12 h at 4° C. The lower sides of transwell filters were blocked with 1% BSA in PBS for 1 h at 37° C. Cells were suspended at a density of $4 \times 10^5$ cells/mL in RPMI 1640 medium containing 0.5% FBS and 0.1% BSA. 100 μL of this suspension was seeded in the upper chamber of the transwell filter. Cells were allowed to migrate for 24 h at 37° C. and then fixed with 10% formalin for 15 min and stained with 0.5% crystal violet. Non-migrated cells in the upper chamber of transwell filters were removed with a cotton swab, viewed under a light microscope, and counted.

As shown in FIG. 1F, human placental laminin promoted cell migration (FIG. 1F). Specifically, rLG1, rLG3 and rLG4 induced cell migration significantly, whereas rLG2 and rLG5 showed no cell migration.

<2-4> Measurement of Biological Activity of rLG Domain Protein Through Neurite Outgrowth Assay Laminin, rLG domain protein, and the peptide were coated onto plates and cells were seeded on the plates in serum-free medium and incubated for 24 h. After changing with serum-free medium again, cells were further cultured for 72 h and neurite outgrowth was examined.

As shown in FIG. 10B, neurite outgrowth was promoted. As shown in FIG. 10B, it was observed that rLG domain protein induced neurite outgrowth in PC12 cells (FIG. 10B).

As a result of biological activity analysis of rLG domain, the biological activity of rLG3 domain protein is similar to laminin in that rLG3 domain protein supports cell adhesion, spreading, migration, and neurite outgrowth.

Experimental Example 3

Characterization of Biological Activities of Ln2-LG3 Peptides

Through the above results of biological activity analysis of the rLG domain proteins, the present inventors found that the biological activity of the rLG3 domain protein is excellent compared to other domains and similar to laminin. Based on these results, the present inventors tried to identify the essential cell binding sequences conferring biological activity of the human LG3 domain protein comprising a 209 residue long polypeptide chain.

<3-1> Synthesis of Ln2-LG3 Peptides

First, the present inventors synthesized six overlapping 12-mer peptides covering amino acids at position 2669 to 2726 derived from the LG3 domain, as shown in FIG. 2A, and tested their biological activities.

All peptides were synthesized by the Fmoc (9-fluorenylmethoxycarbonyl)-based solid-phase methods with a C-terminal amide using a Pioneer peptide synthesizer (Applied Biosystems, Foster City, Calif.), purified, and characterized at the Peptron (Daejon, Korea).

Synthesized 12-mer peptides are as follows:

Ln2-LG3-P1:
(SEQ ID NO: 15)
FQPSPLRNIPPF;

Ln2-LG3-P2:
(SEQ ID NO: 1)
RNIPPFEGCIWN;

Ln2-LG3-P3:
(SEQ ID NO: 16)
KNADIGRCAHQK;

Ln2-LG3-P4:
(SEQ ID NO: 17)
RCAHQKLREDED;

Ln2-LG3-P5:
(SEQ ID NO: 18)
LREDEDGAAPAE;
and

Ln2-LG3-P6:
(SEQ ID NO: 19)
EGCIWNLVINSV.

These synthetic peptides contained the β-sheet strands except for the Ln2-LG3-P1 and the present inventors did not use Ln2-LG3-P6 peptide (amino acids at location 2681 to 2692) in the following experimental examples because the present inventors did not obtain sufficient quantities after purification.

<3-2> Measurement of Cell Adhesion Activity of Ln2-LG3 Peptides

The present inventors used five kinds of Ln2-LG3 peptides synthesized in Experimental example <3-1> and observed their effects on cell adhesion.

First, PC12 cells were cultured on plates coated with varying amounts of five kinds of Ln2-PG3 peptides and then cell adhesion was observed. The peptides were coated in concentrations ranging from 0 to 125 μg/mL on plates by drying them for 12 h at room temperature. Then, PC12 cells were allowed to adhere to the coated plates for 1 h in serum-free medium and cell adhesion was observed in the same way described in Experimental example <2-1>.

As shown in FIG. 2B, the cell adhesion activity of the Ln2-LG3-P2 peptide reached the maximum level at 62.5 μg/mL in PC12 cells. On the other hand, other peptides displayed no cell adhesion activity, even at high coating concentrations (FIG. 2B).

In addition, as a result of measuring the cell adhesion activity of PC12 cells using Ln2-PG3 peptides at a concentration of 62.5 μg/mL where the cell adhesion activity was the maximum, the Ln2-LG3-P2 peptide promoted the cell adhesion of PC12 cells, whereas other peptides displayed no cell adhesion activity, as shown in FIG. 2C.

<3-3> Measurement of the Effect of Ln2-LG3 Peptides on Cell Spreading, Migration, and Neurite Outgrowth Promotion The present inventors used five kinds of Ln2-LG3 peptides and observed their effects on cell spreading, migration, and neurite outgrowth.

The present inventors compared the cellular activities of Ln2-LG3-P2 peptide to scrambled peptide (SEQ ID NO:20, NWEIRCIPGNPF) of Ln2-LG3-P2 peptide and Ln2-LG3-P1 peptide to Ln2-LG3-P5 peptide at a concentration of 62.5 μg/mL where the cell adhesion activity was the maximum. Specifically, PC12 cells were cultured on plates coated with laminin (5 μg/mL), rLG3 (25 μg/mL), Ln2-LG3-P1 (62.5 μg/mL), Ln2-LG3-P2 (62.5 μg/mL), Ln2-LG3-P3 (62.5 μg/mL), Ln2-LG3-P4 (62.5 μg/mL), Ln2-LG3-P5 (62.5 μg/mL), and SP (Scrambled peptide, SEQ ID NO:20) (62.5 μg/mL) for 1 h in serum-free medium and the cell adhesion was observed. PC12 cells were cultured on plates which were coated in the same way for 3 h in serum-free medium and the cell spreading was observed.

As shown in FIGS. 2D and 2E, Ln2-LG3-P2 peptide influenced cell spreading and migration comparable to that of rLG3, respectively, whereas other peptides including the scrambled peptide (SEQ ID NO:20) were entirely ineffective in promoting cell spreading and migration (FIG. 2D and FIG. 2E).

<3-4> Measurement of the Effect of Ln2-LG3 Peptides on Cell Spreading, Migration, and Neurite Outgrowth in Schwann Cells Because the Ln2-LG3-P2 peptide of the present invention showed cell adhesion activity in PC12 cells in Experimental example <3-1>, the present inventors used Schwann cells that play a central role in nerve regeneration to identify whether the Ln2-LG3-P2 peptide of the present invention would also mediate adhesion of other types of cells.

Specifically, Schwann cells were cultured on plates coated with laminin (5 µg/mL), rLG3 (25 µg/mL), Ln2-LG3-P1 (62.5 µg/mL), Ln2-LG3-P2 (62.5 µg/mL), Ln2-LG3-P3 (62.5 µg/mL), Ln2-LG3-P4 (62.5 µg/mL), Ln2-LG3-P5 (62.5 µg/mL), and SP (Scrambled peptide, SEQ ID NO:20) (62.5 µg/mL) for 1 h in serum-free medium and the cell adhesion of Schwann cells was observed. Schwann cells were cultured on plates which were coated in the same way for 3 h in serum-free medium and the cell spreading of Schwann cells was observed.

As shown in FIG. 2F, the Ln2-LG3-P2 peptide of the present invention had a strong effect on Schwann cell adhesion relative to BSA, scrambled peptide, or other Ln2-LG3 peptides. The cell adhesion activity to the Ln2-LG3-P2 peptide of the present invention was similar to that of laminin (FIG. 2F).

In addition, as shown in FIG. 2G, although Schwann cell spreading on the Ln2-LG3-P2 peptide was reduced by approximately 50% compared to laminin, the Ln2-LG3-P2 peptide showed substantially higher spreading than BSA or scrambled peptide, demonstrating that the Ln2-LG3-P2 peptide is functionally active in promoting Schwann cell adhesion and spreading (FIG. 2G).

<3-5> Comparison of Cell Adhesion Activity, Spreading, and Neurite Outgrowth of Ln2-LG3 Peptides in Various Cells The present inventors used PC12, CV-1, NIH/3T3, normal human epidermal keratinocytes (NHEK), normal human oral keratinocytes (NHOK), and normal human dermal fibroblasts (NHDF) to measure effects of the Ln2-LG3-P2 peptide of the present invention on cell adhesion activity, spreading, migration, and neurite outgrowth promotion in various cells.

The skin-derived precursor-derived, differentiated Schwann cells used in the present invention did not migrate in the transwell migration chamber assay system used in the present invention, possibly due to extensive neurite branching and outgrowth already present in the cells.

Specifically, normal human epidermal keratinocytes (NHEK), normal human oral keratinocytes (NHOK), normal human dermal fibroblasts (NHDF), CV-1, and NIH/3T3 cells which were cultured in <Example 1> were cultured on plates coated with Ln2-LG3-P2 (62.5 µg/mL) in serum-free media for 1 h and then, each cell adhesion was observed.

As shown in FIG. 2H, the Ln2-LG3-P2 peptide at 62.5 µg/mL displayed a strong cell adhesion activity to normal human epidermal keratinocytes at passage 2, normal human oral keratinocytes at passage 2, and normal human dermal fibroblasts at passage 4. In addition, the Ln2-LG3-P2 peptide at 62.5 µg/mL displayed a strong cell adhesion activity in CV-1 and NIH/3T3 cells. These results mean that the Ln2-LG3-P2 peptide of the present invention exhibits cell adhesion activity in various cells (FIG. 2H).

<3-6> Examination of the Effect of the Ln2-LG3-P2 Peptide on Cell Adhesion, Spreading, Migration, and Neurite Outgrowth Through Cell Adhesion Inhibition Assay The ability of the Ln2-LG3-P2 peptide to compete for cell adhesion, spreading, migration, and neurite outgrowth promotion to rLG3 protein was examined to verify the role of the Ln2-LG3-P2 peptide in the cellular activities of LG3 domain of human laminin α2 chain.

<3-6-1> Examination of Dose-Dependent Inhibitive Effect of Ln2-LG3-P2 Peptide Pretreatment on Cell Adhesion in PC12 Cells Specifically, PC12 cells were pretreated with the Ln2-LG3-P2 peptide in concentrations of 0, 0.2, 0.4, 0.6, 0.8, 1.0, or 1.2 µg/mL for 10 min at room temperature and then cultured on plates coated with rLG3 (25 µg/mL) for 1 h in serum-free medium.

As shown in FIG. 11A, cell adhesion in the group pretreated with Ln2-LG3-P2 peptide decreased in a dose-dependent manner in comparison with the group pretreated without Ln2-LG3-P2 peptide (FIG. 11A). Values shown in FIG. 11A are expressed as a percentage of the value for cells of the group pretreated without Ln2-LG3-P2 peptide (mean±S.D., n=4).

<3-6-2> Examination of Inhibitive Effect of Ln2-LG3-P2 Peptide Pretreatment on Cell Adhesion, Spreading, Migration, and Neurite Outgrowth Promotion in PC12 Cells PC12 cells were pretreated with 500 µg/mL of Ln2-LG3-P1, Ln2-LG3-P2, Ln2-LG3-P3, Ln2-LG3-P4, Ln2-LG3-P5 and SP (scramble peptide) (SEQ ID NO:20) for 10 min at room temperature and then cultured on plates coated with rLG3 (25 µg/mL) in serum-free medium. To observe cell adhesion, PC12 cells were incubated on the coated plates for 1 h and to observe cell spreading, PC12 cells were incubated on the coated plates for 3 h. To observe cell migration, cells were seed into the upper chamber of transwell filters coated with rLG3 (25 µg/mL) and cultured for 24 h. Cell migration was quantified by counting the number of cells that had migrated through the filter.

As shown in FIGS. 11A to 11D, the Ln2-LG3-P2 peptide inhibited cell adhesion to rLG3 protein in a dose-dependent manner with inhibition of approximately 40% observed at 500 µg/mL. The Ln2-LG3-P2 peptide also inhibited cell spreading and migration to rLG3 protein (FIG. 11C and FIG. 11D). Taken together, these results suggest that the Ln2-LG3-P2 peptide within the LG3 domain is important for cell adhesion, spreading, migration, and neurite outgrowth of PC12 cells.

Data shown in FIGS. 11B to 11D are expressed as a percentage of the value for cells of the group pretreated without Ln2-LG3-P2 peptide. Values are expressed as the mean±S.D. (n=4).

Experimental Example 4

Examination of the Effect of Arg Residue of Ln2-LG3-P2 Peptide on Cellular Activities <4-1> Preparation of Mutant rLG1 Protein (rLG3-M1)

The present inventors and other researchers have previously demonstrated that charged amino acid residues, such as Arg residue, are necessary for cell adhesion (Kim, J. M., et al., *Exp. Cell Res.*, 2005; Hohenester, E., et al., *Mol. Cell*, 1999). Because charged amino acid residues are important for the interaction between the LG domains of some laminin α chains and integrins, syndecan-1, or heparin-like cell surface receptors, mutant rLG1 protein (rLG3-M1) (SEQ ID NO:21, ANIPPFEGCIWN) was expressed by substituting the positively charged Arg in the Ln2-LG3-P2 site with Ala and then was obtained and used in the following experiments (FIG. 3A).

<4-2> Analysis of Location of Ln2-LG3-P2 Peptide in the LG Domain

The space-filling model and ribbon diagram illustrated that Ln2-LG3-P2 lied on the surface of the LG3 domain (Carafoli, F., et al., *J. Biol. Chem.*, 2009). In particular, basic amino acid residue Arg in the Ln2-LG3-P2 was found in loop, exposed on the surfaces of protein and thus well situated to participate in protein-protein interactions, such between laminin and cell surface receptors (FIG. 12).

<4-3> Examination of the Effect of Mutant rLG3 Protein (rLG3-M1) on Cell Adhesion, Spreading, Migration, and Neurite Outgrowth The mutant rLG3-M1 peptide expressed by substituting Arg with Ala in Experimental example <4-1> showed about 27 kDa of size (FIG. 3B).

The present inventors observed the effect of mutant rLG3-M1 protein prepared through site-direct mutant on cell adhesion, spreading, migration, and neurite outgrowth promotion.

Specifically, to observe cell adhesion, spreading, migration, and neurite outgrowth promotion, the methods described in Experimental examples <2-1> to <2-3> were used and PC12 cells were cultured on plates coated with laminin (5 µg/mL), rLG3 (25 µg/mL), and rLG3-M1 (25 µg/mL) and observed. To observe cell adhesion, PC12 cells were incubated on the coated plates for 1 h and to observe cell spreading, PC12 cells were incubated on the coated plates for 3 h. To observe cell migration, PC12 cells were incubated on the coated plates for 1 h and analyzed.

As shown in FIGS. 3C to 3E, the mutant rLG3-M1 peptide showed significantly reduced levels of cell adhesion, spreading, migration, and neurite outgrowth compared with rLG3 protein (the Ln2-LG3-P2 peptide) in PC12 cells (FIGS. 3C, 3D, and 3E).

In addition, PC12 cells were pretreated with rLG3 (250 or 500 µg/mL) or vehicle (phosphate buffer, pH 3.0) for 30 min and then seeded on plates coated with laminin (5 µg/mL) for 30 min in serum-free medium and cell adhesion was observed.

As shown in FIG. 3F, mutant rLG3-M1 peptide did not inhibit cell adhesion to laminin in PC12 cells pretreated with the peptide at 250 µg/mL concentration (FIG. 3F). Meanwhile, rLG3 showed weak inhibition of cell adhesion to laminin by 23% in PC12 cells pretreated with 250 µg/mL of the peptide; however, rLG3 inhibited cell adhesion to laminin by 48% in PC12 cells pretreated with 500 µg/mL of the peptide.

This suggests that other cell surface receptors induce cell adhesion to laminin and that integrins, α-dystroglycan, and syndecan-1 bind laminin α2 chain LG domains, in agreement with previous reports (Suzuki, N., et al., *Connect. Tissue Res.*, 2005; Jung, S. Y, et al., *J. Biol. Chem.*, 2009; Smirnov, S. P., et al., *J. Biol. Chem.*, 2002).

<4-4> Comparison of Laminin-1 and Laminin-2 from Different Species

Comparison of laminin-1 and laminin-2 from different species show that several residues in the Ln2-LG3-P2 peptide, including the basic amino acid residues, Arg/Lys residues, are highly conserved (FIG. 3G and Table 1).

TABLE 1

Comparison of laminin-1 and laminin-2 from different species

| Species | Peptide type | Amino acid sequence | SEQ ID NO |
|---|---|---|---|
| Human | Ln-2 | R N I P P F EGC I WN | SEQ ID NO: 22 |
| Mouse | Ln-2 | R N I P A F QGC VWN | SEQ ID NO: 23 |
| Rat | Ln-2 | R N I P A F QGC VWN | SEQ ID NO: 24 |
| Chicken | Ln-2 | R N I P P F EGC I WN | SEQ ID NO: 25 |
| Globefish | Ln-2 | R V N V P F QGC I WN | SEQ ID NO: 26 |
| Danio | Ln-2 | R P S V P F EGC I WN | SEQ ID NO: 27 |
| Human | Ln-1 | T MR R S F HGC I K N | SEQ ID NO: 28 |
| Mouse | Ln-1 | K M R T S F HGC I K N | SEQ ID NO: 29 |
| Rat | Ln-1 | R M R T S F HGC I K N | SEQ ID NO: 30 |
| Horse | Ln-1 | R M R G S F HGC I R N | SEQ ID NO: 31 |
| Dog | Ln-1 | K MR K S F HGC I K N | SEQ ID NO: 32 |
| Chicken | Ln-1 | KM T GS F YGC I SN | SEQ ID NO: 33 |
| Danio | Ln-1 | T L T P A F YGC I R N | SEQ ID NO: 34 |

<4-5> Examination of the Effect of Synthetic Ln2-LG3-P2A Peptide on Cell Adhesion To investigate the role of Arg residue in the Ln2-LG3-P2 peptide, Ln2-LG3-P2A peptide was synthesized by substituting Arg in p2 site of recombinant protein rLG3 with Ala. PC12 cells were seeded on plates coated with Ln2-LG3-P2A peptide synthesized by substituting Arg in Ln2-LG3-P2 peptide with Ala and cell adhesion activity was compared.

Specifically, PC12 cells were pretreated with Ln2-LG2-P2 (500 µg/mL) and Ln2-LG3-P2A (500 µg/mL) and then, cell adhesion was observed on plates coated with rLG3 (25 µg/mL).

As shown in FIG. 3H, the cell adhesion was significantly inhibited by mutant Ln2-LG3-P2A peptide compared to the control group Ln2-LG3-P2. As shown in FIG. 3I, Ln2-LG3-P2A did not inhibit cell adhesion to rLG3 in PC12 cells pretreated with the peptide at 500 µg/mL.

Taken together, these results suggest that the Ln2-LG3-P2 peptide functions as a cell-binding site in the human laminin α2 LG3 domain and that charged amino acid residue Arg in the Ln2-LG3-P2 peptide is essential for the biological activity of the peptide.

Experimental Example 5

Identification of the Receptors for the Human Laminin α2 LG3 Domain

<5-1> Examination of the Effect of Metal Chelating Reagent Treatment on Cell Adhesion and Spreading to LG3 Domain and the Ln2-LG3-P2 Peptide Because the identities of the receptors for the human laminin α2 LG3 domain have not been fully elucidated, the present inventors designed a set of experiments to identify the specific adhesion receptor for LG3 and Ln2-LG3-P2 that may mediate the adhesion of PC12 cells. Binding of integrins and α-dystroglycan to their ligands is known to require a divalent cation, such as $Ca^{2+}$ and $Mn^{2+}$ (Hall, H., et al., *Mol. Cell. Neurosci.*, 2003). To determine the role of divalent cations, the present inventors studied the effect of EDTA, a metal-chelating reagent, on cell adhesion and spreading to laminin, LG3 domain, and the Ln2-LG3-P2 peptide.

PC12 cells were pretreated with either 5 mM EDTA or 1 mM $MnCl_2$ for 15 min at 37° C. and seeded on plates coated with rLG3 or the Ln2-LG3-P2 peptide. To measure cell adhesion, PC12 cells were incubated on the coated plates for 1 h and absorbance was measured. To measure cell spreading, PC12 cells were incubated on the coated plates for 3 h and relative cell area was measured using Image-Pro Plus software.

Cell adhesion and spreading to laminin were completely inhibited in PC12 cells cultured in the presence of 5 mM EDTA compared with cells of the control group pretreated without EDTA, but cell adhesion and spreading to rLG3 or Ln2-LG3-P2 were partially inhibited by EDTA pretreatment (FIG. 4A and FIG. 4B). In contrast, pretreatment of $Mn^{2+}$ significantly enhanced cell adhesion and spreading to laminin, rLG3, and Ln2-LG3-P2 (FIG. 4A and FIG. 4B).

<5-2> Examination of the Effect of Integrin Antibody Treatment on Cell Adhesion, Spreading, Migration and Neurite Outgrowth Promotion A previous report demonstrated that PC12 cells express two major integrins, α1β1 and α3β1, which interact with laminin at a spatially distinct site (Tomaselli, K. J., et al., *Neuron*, 1990). To better understand the interaction of rLG3 and the Ln2-LG3-P2 peptide with integrins, the present inventors examined the effect of monoclonal function-blocking antibody against the integrin α1, α3, and β1 subunits as a competitor for cell adhesion, spreading, migration, and neurite outgrowth.

Specifically, PC12 cells were pretreated with either 5 mM EDTA or 10 μg/mL of function-blocking monoclonal antibodies against integrin α1 (Ha31/8; BD Biosciences, San Jose, Calif.), ingegrin α3 (Ralph 3.2; Santa Cruz Biotechnology, Santa Cruz, Calif.) and β1 (Ha2/5; BD Biosciences) subunits for 15 min at 37° C. and preincubated. Then, the preincubated cells were coated in well plates precoated with 500 μL of laminin (5 μg/mL) or rLG3 domain protein (25 μg/mL) for 1 h and the Ln2-LG3-P2 peptide (25 μg/well) was also coated in well plates.

Integrin α3 and β1 antibodies partially inhibited cell adhesion, spreading, migration, and neurite outgrowth to rLG3 and Ln2-LG3-P2 relative to PC12 cells pretreated without EDTA or integrin antibody (the control group), but the integrin α1 antibody was entirely ineffective in this assay (FIGS. 4C to 4E). Values shown in FIGS. 4C to 4E are expressed as the mean±S.D. (n=3).

These results indicate that α3β1 integrin is a cellular receptor of rLG3 and Ln2-LG3-P2 that affect the cell adhesion, spreading, migration, and neurite outgrowth promotion activities.

Experimental Example 6

Identification of the Biologically Active Core Sequence in the Ln2-LG3-P2 Peptide <6-1> Synthetic Peptides that are N- and C-Terminal Truncated or Added Peptides of the Ln2-LG3-P2 Peptide From the above stated experimental examples, it was observed that the Ln2-LG3-P2 peptide binds to α3β1 integrin and promotes cell adhesion, spreading, migration, and neurite outgrowth. To determine the biologically active core sequence in the Ln2-LG3-P2 peptide, synthetic peptides that are N- and C-terminal truncated or C-terminal added peptides of the Ln2-LG3-P2 peptide were prepared (FIG. 5A)

TABLE 2

Synthetic peptides that are N- and C-terminal truncated or C-terminal added peptides of the Ln2-LG3-P2 peptide

| Name of peptide | Amino acid sequence | SEQ ID NO |
|---|---|---|
| Ln2-LG3-P2 | RNIPPFEGCIWN | SEQ ID NO: 1 |
| Ln2-LG3-P2-DN1 | NIPPFEGCIWN | SEQ ID NO: 35 |
| Ln2-LG3-P2-DN2 | IPPFEGCIWN | SEQ ID NO: 36 |
| Ln2-LG3-P2-DN3 | PPFEGCIWN | SEQ ID NO: 37 |
| Ln2-LG3-P2-DN4 | PFEGCIWN | SEQ ID NO: 38 |
| Ln2-LG3-P2-DN5 | FEGCIWN | SEQ ID NO: 39 |
| Ln2-LG3-P2-DC1 | RNIPPFEGCIW | SEQ ID NO: 40 |
| Ln2-LG3-P2-DC2 | RNIPPFEGCI | SEQ ID NO: 41 |
| Ln2-LG3-P2-DC3 | RNIPPFEGC | SEQ ID NO: 42 |
| Ln2-LG3-P2-DN3-DC1 | PPFEGCIW | SEQ ID NO: 43 |

TABLE 2-continued

Synthetic peptides that are N- and C-terminal truncated or C-terminal added peptides of the Ln2-LG3-P2 peptide

| Name of peptide | Amino acid sequence | SEQ ID NO |
|---|---|---|
| Ln2-LG3-P2-DN3-DC2 | PPFEGCI | SEQ ID NO: 44 |
| Ln2-LG3-P2-DN3-DC3 | PPFEGC | SEQ ID NO: 45 |
| Ln2-LG3-P2-DN3-DC4 | PPFEG | SEQ ID NO: 46 |
| Ln2-LG3-P2-DN3-DC5 | PPFE | SEQ ID NO: 47 |
| Ln2-LG3-P2-DN3-DC6 | PPF | SEQ ID NO: 48 |
| Ln2-LG3-P2-AC1 | RNIPPFEGCIWNLVINSVPMDFAR | SEQ ID NO: 49 |
| Ln2-LG3-P2-AC2 | RNIPPFEGCIWNLVINSVPMDFARPVSFKNADIGRC | SEQ ID NO: 50 |

<6-2> Examination of the Effect of N- and C-Terminal Truncated or Added Ln2-LG3-P2 Peptide on Cell Adhesion, Spreading, Migration and Neurite Outgrowth Promotion To measure cell adhesion, spreading, migration, and neurite outgrowth promotive activities of PC12 cells using the prepared synthetic peptides that are N- and C-terminal truncated or C-terminal added peptides of the Ln2-LG3-P2 peptide, peptides described in Table 1 were coated onto plates at 62.5 μg/mL and PC12 cells were seeded thereon.

Ln2-LG3-P2 and scrambled peptide were used as the positive and negative controls, respectively. All peptides except Ln2-LG3-P2-DN3, Ln2-LG3-P2-DN4, and Ln2-LG3-P2-DC1 showed a significantly lower cell adhesion activity than the Ln2-LG3-P2 control (FIG. 5B). Likewise, cell spreading activity of Ln2-LG3-P2-DN3 and Ln2-LG3-P2-DN4 was similar to Ln2-LG3-P2 (FIG. 5C).

Cell migration activity of Ln2-LG3-P2-DN3 was also similar to Ln2-LG3-P2, but Ln2-LG3-P2-DN4 did not show cell migration activity (FIG. 5D). Values shown in FIG. 5C and FIG. 5D are expressed as the mean±S.D. (n=4). P value is expressed on the basis of the measured value for cells incubated on plates coated with BSA or scrambled peptide (SP)

Experimental Example 7

Examination of Integrin-Mediated Cell Adhesion Induction by the Ln2-LG3-P2 Peptide Integrin-mediated cell adhesion is known to induce actin stress fiber formation and focal adhesion assembly (Clark, E. A., et al., Science, 1995; Schwartz, M. A. et al., Annu. Rev. Cell Dev. Biol., 1995). Therefore, to further evaluate whether rLG3 and the Ln2-LG3-P2 peptide are able to induce integrins-mediated cell adhesion, the present inventors examined by immunostaining the organization of actin stress fibers and localization to focal adhesions of PC12 cells.

Specifically, for immunostaining, PC12 cells were incubated on Lab-Tek chamber slides (Nalge Nunc International, Rochester, N.Y.) coated with laminin (5 μg/mL), rLG domain proteins (25 μg/mL), or Scrambled peptide (SP) (25 μg/well) in serum-free medium for 3 h at 37° C. Lab-Tek chamber slides were coated with BSA for the control. After rinsing with PBS, PC12 cells were fixed with 3.7% formalin for 20 min and permeabilized with 0.5% Triton X-100 for 5 min. PC12 cells were incubated with primary antibodies for 12 h at 4° C. The primary antibodies used were 1:500 anti-vinculin (Sigma-Aldrich 9131), or 1:300 rhodamin-phalloidin (Invitrogen R154) antibodies. After rinsing with PBS, PC12 cells were immunostained with FITC-conjugated anti-mouse IgG antibody (Jackson ImmunoResearch Laboratories, West Grove, Pa.) or rhodamin-conjugated anti-mouse IgG antibody (Santa Cruz Biotechnology) for 1 h at room temperature. After being washed three times with PBS, the stained PC12 cells were mounted and photographed using a confocal laser scanning microscope (FV300; Olympus, Japan).

As shown in FIG. 6A and FIG. 6B, PC12 cells on laminin spread very well and formed actin stress fibers and focal adhesions. Similarly, PC12 cells on rLG3 and Ln2-LG3-P2 also spread well, formed stress fiber formation, and focal adhesions but to a lesser degree than those on laminin (FIG. 6A and FIG. 6B).

In contrast, other rLG domain proteins and scrambled peptide had no effect on spreading of PC12 cells and did not organize actin stress fibers (FIG. 6A and FIG. 6B). For reference, bar shown in a photograph of immunostaining in FIG. 6A is 50 μm and bar shown in a photograph of immunostaining in FIG. 6B is 20 μm.

Experimental Example 8

Examination of FAK Phosphorylation by the Interaction of Ln2-LG3-P2 Peptide and α3β1 Integrin Previous studies identified that FAK is a component of an integrin-mediated signal transduction pathway (Clark, E. A., et al., Science, 1995; Schwartz, M. A., et al., Annu. Rev. Cell Dev. Biol., 1995). A hallmark of FAK activation is a rapid phosphorylation of Tyr-397 upon integrin-mediated cell adhesion and spreading (Richardson, A., et al., Nature, 1996). Using phospho-FAK-Tyr397 antibody, the present inventors examined FAK phosphorylation levels in PC12 cells plated on laminin, rLG3, and Ln2-LG3-P2.

For measuring FAK phosphorylation, specifically, PC12 cells were starved for 12 h by replacing RPMI 1640 medium with 0.1% FBS. PC12 cells ($2 \times 10^6$ cells) were plated on 60-mm dishes precoated with laminin (5 μg/mL), rLG3 (25 μg/mL), or Ln2-LG3-P2 (25 μg/well), and allowed to adhere for the indicated times (15 min, 30 min, and 60 min). Cells were washed with ice-cold PBS and lysed with 200 μL of RIPA buffer (50 mM Tris-HCl, pH 7.4, 150 mM NaCl, 1 mM EDTA 1% Triton X-100, 1 mM PMSF, 2 mM $Na_3VO_4$, 1 mM glycerol phosphate) containing a protease inhibitor cocktail. RIPA lysates were denatured using SDS sample buffer (50 mM Tris/HCl, pH 6.8, 2% SDS, 10% glycerol, 0.1% bromophenol blue, 50 mM dithiothreitol) and analysed by SDS- PAGE. The separated proteins were electroblotted onto an Immobilon-P membrane (Millipore, Bedford, Mass.) and probed with primary antibodies to FAK Tyr-397 (Biosource, Camarillo, Calif.), FAK (Upstate Biotechnology Inc., Lake Placid, N.Y.). All blots were then detected with HRP-conjugated secondary antibodies (Cell Signaling). Signals were detected by ECL (iNtRON Biotechnology, Korea).

As shown in FIG. 6C, the FAK phosphorylation levels at Tyr-397 peaked at 15 min in PC12 cells seeded on laminin, rLG3, and Ln2-LG3-P2, and decreased at 30 min or 60 min. Overall, these results suggest that α3β1 integrin binding to laminin, LG3 domain peptide, and the Ln2-LG3-P2 peptide is critical for formation of stress fibers and focal adhesions. The Ln2-LG3-P2 peptide is sufficient for the interaction with α3β1 integrin and for the integrin-mediated stimulation of FAK phosphorylation at Tyr-397 (FIG. 6C).

Experimental Example 9

Measurement of Translocation of PKCδ to Integrin β1 and Phosphorylation of PKCδ by the Interaction of Ln2-LG3-P2 Peptide and α3β1 Integrin <9-1> Examination of Correlation Between PKC Activity and Ln2-LG3-P2 Mediated Cell Adhesion Cell spreading and focal adhesion formation are known to be promoted by PKC activation (Lewis, J. M., et al., *J. Cell Biol.*, 1996; Ron, D., et al., *FASEB J.*, 1999; Huang, X., et al., *J. Cell Sci.*, 1998). Therefore, the present inventors investigated whether PKC is involved in laminin-, rLG3-, and Ln2-LG3-P2-mediated cell adhesion.

PC12 cells were pretreated with 0.05 μM, 0.1 μM, and 0.5 μM of calphostin C for 15 min at 37° C. and then incubated on plates coated with rLG3 or the Ln2-LG3-P2 peptide for 1 h.

As shown in FIG. 7A, cell adhesion activities to laminin, rLG3, and Ln2-LG3-P2 were significantly inhibited in a dose-dependent manner in PC12 cells pretreated with calphostin C, an inhibitor of PKC, indicating that PKC is required for integrin-mediated adhesion of PC12 cells (FIG. 7A). Data are expressed as a percentage of the value for cells preincubated without calphostin C (mean±S.D., n=3).

In addition, calphostin C did not affect cell growth at the indicated concentrations and duration of treatment (data not shown), suggesting that the inhibition of cell adhesion to laminin, rLG3, and the Ln2-LG3-P2 peptide is not caused by cellular cytotoxicity.

<9-2> Examination of the Subcellular Distributions of PKC Isoforms Upon Cell Adhesion Because stimulation using 0.2% fetal calf serum treatment of mouse Swiss 3T3 fibroblasts leads to the redistribution of PKCδ to focal adhesions (Barry, S. T., et al., *J. Cell Sci.*, 1994), the present inventors examined the subcellular distributions of PKC isoforms of PC12 cells seeded on laminin-coated dishes by immunostaining.

PC12 cells were plated on laminin-coated glass slides for 30 min in serum-free medium. The cells were immunostained with the anti-PKCα or δ antibodies and rhodamine-phalloidin.

PKCα and -δ colocalized with F-actin in peripheral regions of the cells (FIG. 7B). The arrows shown in FIG. 7B indicate the ends of stress fibers and bar is 20 μm.

These two PKC isoforms were found at the ends of actin stress fibers, well situated to regulate integrin-mediated cell adhesion and spreading.

<9-3> Examination of Translocation of PKCα and -δ to Integrin β1 Upon Cell Adhesion To identify whether PKCα and -δ would be translocated to integrin β1, the present inventors tested by immunoprecipitation using anti-His$_6$-tag antibody or anti-integrin β1 antibody whether PKCα and -δ exist as associated complexes in PC12 cells seeded on laminin-, rLG3-, and Ln2-LG3-P2-coated dishes.

Specifically, for immunoprecipitation, PC12 cells were starved for 12 h with RPMI 1640 medium containing 0.1% FBS. Cells were detached and resuspended in serum-free medium with 0.1% BSA. PC12 cells (4×10$^6$ cells/100-mm dish) were seeded on laminin (5 μg/mL)-, rLG3 (25 μg/mL)-, or Ln2-LG3-P2 (25 μg/well)-coated dishes and allowed to attach for 30 min at 37° C. After incubation, cells were washed with ice-cold PBS, lysed with RIPA buffer containing a protease inhibitor cocktail. The lysates were centrifuged and the supernatants were preincubated with 50 μL of immobilized protein G beads (Upstate Biotechnology Inc.) for 1 h at 4° C. to remove nonspecific binding. The supernatants were incubated with anti-His$_6$ (Roche, Mannheim, Germany), anti-integrin (Santa Cruz Biotechnology), or anti-PKCδ (Santa Cruz Biotechnology) antibodies for 2 h at 4° C. The immunocomplexes were precipitated with immobilized protein G beads for 12 h at 4° C. After centrifugation, beads carrying the immune complexes were washed four times with RIPA buffer. Immunoprecipitates were resuspended in SDS sample buffer, boiled for 5 min, and analysed by Western blotting.

As shown in FIG. 7C, in anti-His$_6$ immunoprecipitates, PKCα, PKCδ, and FAK were observed in cells seeded on the rLG3 (His-tagged fusion protein)-coated dishes (FIG. 7C).

Similarly, in integrin β1 immunoprecipitates, PKCα, PKCδ, and FAK were also observed in cells seeded on laminin-, rLG3-, and Ln2-LG3-P2-coated dishes (FIG. 7D).

<9-4> Examination of Colocalization of Integrin β1 with PKCα or PKCδ

PC12 cells were seeded on glass slide chambers coated with laminin, rLG3, or the Ln2-LG3-P2 peptide for 30 min and immunostained with anti-integrin β1 antibody and anti-PKCδ antibody.

Immunofluorescence analysis showed the colocalization of PKCδ with integrin β1 (FIG. 7E).

In addition, PC12 cells were seeded on glass slide chambers coated with laminin, rLG3, or the Ln2-LG3-P2 peptide for 30 min and immunostained with anti-integrin β1 antibody and anti-PKCα antibody and the colocalization of PKCα with integrin β1 was observed (FIG. 13).

<9-5> Examination of the Tyrosine Phosphorylation of PKCδ Upon Cell Adhesion

Because adhesion of Cos7 monkey fibroblasts to fibronectin is known to promote tyrosine phosphorylation of membrane-associated PKCδ (Miranti, C. K., et al., *J. Biol. Chem.*, 1999), the present inventors tested whether the tyrosine phosphorylation of PKCδ would be affected by laminin, rLG3, and the Ln2-LG3-P2 peptide in PC12 cells.

PC12 cells were incubated on dishes coated with laminin, rLG3, or the Ln2-LG3-P2 peptide for 30 min and the interaction of PKCδ with phosphotyrosine was examined using immunoprecipitation and Western blotting.

As shown in FIG. 7F, cell adhesion of PC12 cells to laminin, rLG3, and the Ln2-LG3-P2 peptide increased tyrosine phosphorylation of PKCδ (FIG. 7F).

Taken together, these results indicate that receptor-ligand interaction of α3β1 integrin with laminin, rLG3, and the Ln2-LG3-P2 peptide induces translocation of PKCδ to the complex with integrin β1 and tyrosine phosphorylation of PKCδ.

Experimental Example 10

Functional Roles of PKCα and PKCδ in Cell Adhesion, Spreading, Migration, Stress Fiber Formation, and FAK Phosphorylation at Tyr-397 of the Ln2-LG3-P2 Peptide <10-1> Examination of the Effect of PKC Inhibitor on Cell Adhesion, Spreading, Migration, and Stress Fiber Formation The present inventors examined the functional roles of PKCα and PKCδ in cell adhesion, spreading, migration, and stress fiber formation using specific pharmacological inhibitors: PKCα/β inhibitor Gö6976 ($IC_{50}$=2.3 nM) or the PKCδ inhibitor rottlerin ($IC_{50}$=3-6 μM).

PC12 cells were pretreated with Gö6976 or rottlerin for 15 min at 37° C. and seeded on laminin-, rLG3-, or Ln2-LG3-P2-coated plates and then, cell adhesion, spreading, migration, and stress fiber formation were observed. To observe cell adhesion, the pretreated PC12 cells were incubated for 1 h and to observe cell spreading and stress fiber formation, the pretreated PC12 cells were incubated on the coated plates for 3 h. In addition, to observe cell migration, the pretreated PC12 cells were incubated on the coated plates for 24 h.

As shown in FIGS. 8A to 8D, treatment with the PKCδ inhibitor rottlerin but not with Gö6976 significantly impaired adhesion, spreading, migration, and stress fiber formation of PC12 cells to laminin, rLG3, and the Ln2-LG3-P2 peptide (FIGS. 8A to 8D). In addition, Gö6976 and rottlerin did not affect cell viability at the concentrations used and duration of treatment.

These results clearly indicate that the PKCδ signaling is associated with laminin-, rLG3-, and Ln2-LG3-P2-mediated cell adhesion, spreading, migration, and stress fiber formation of PC12 cells.

<10-2> Examination of the Effect of Rho-Kinase Inhibitor on Cell Adhesion, Spreading, Migration, and Stress Fiber Formation Because stress fiber formation is dependent on the activation of Rho-kinase in fibroblasts (Katoh, K., et al., *Genes Cells,* 2007), the present inventors examined stress fiber formation in the presence of a Rho-kinase inhibitor Y27632.

PC12 cells were seeded on glass slide chambers coated with laminin, rLG3, or Ln2-LG3-P2 for 1 h. The cells were treated with 10 μm Y27632, a selective inhibitor of Rho-associated protein kinase, for 2 h in serum-free medium and immunostained with rhodamine-phalloidin.

The present inventors observed that 10 μM Y27632 treatment completely disassembled stress fibers of PC12 cells to laminin, rLG3, and the Ln2-LG3-P2 peptide (FIG. 14A).

In addition, to determine the effect of PKCδ inhibitor rottlerin in the stress fiber formation of cells to laminin, rLG3, and Ln2-LG3-P2, the present inventors treated PC12 cells with 5 μM rottlerin and observed the stress fiber formation.

PC12 cells were seeded on glass slide chambers coated with laminin, rLG3, or Ln2-LG3-P2. After 2.5 h incubation, the cells were treated with 5 μM rottlerin for 30 min and immunostained with rhodamine-phalloidin.

As shown in FIG. 14B, rottlerin treatment did not interfere with stress fiber formation of PC12 cells already spread on laminin, rLG3, and Ln2-LG3-P2 (FIG. 14B). The graphs shown in FIG. 14A and FIG. 14B show the percentage of cells with actin stress fibers and data are expressed as mean±S.D. (n=3). Bars shown in FIG. 14A and FIG. 14B are 20 μm.

This finding is consistent with a previous report that rottlerin (1-3 μM) treatment does not impair stress fiber formation of fibroblasts pre-spread on fibronectin (Dovas, A., et al., *J. Cell Sci.,* 2006).

<10-3> Examination of the Effect of PKC Inhibitor on FAK Phosphorylation at Tyr-397

A previous report showed that muscle cell spreading and FAK phosphorylation on fibronectin are blocked by inhibitors of PKC (Disatnik, M. H., et al., *J. Cell Sci.,* 2002). Thus, the present inventors examined the effects of the PKCα/β inhibitor Gö6976 and the PKCδ inhibitor rottlerin on FAK tyrosine phosphorylation.

PC12 cells were pretreated with 5 nM Gö6976 or 5 μM rottlerin for 15 min at 37° C. and seeded on laminin-, rLG3-, or Ln2-LG3-P2-coated plates for 15 min in serum-free medium.

As shown in FIG. 8B, rottlerin treatment reduced the level of FAK phosphorylation at Tyr-397 in PC12 cells seeded on plates coated with laminin, rLG3, and Ln2-LG3-P2; however, Gö6976 treatment did not affect the level of FAK phosphorylation at Tyr-397 (FIG. 8B).

Taken together, these results indicate that PKCδ is important for the initial adhesion and spreading of PC12 cells seeded on laminin, rLG3, and Ln2-LG3-P2 in a Rho-kinase-dependent pathway and that PKCδ activation is necessary for cell adhesion, spreading, migration, and FAK phosphorylation at Tyr-397 on laminin, rLG3, and Ln2-LG3-P2.

<10-4> Examination of the Effect of PLC Inhibitor on Cell Adhesion and Spreading PKC activation is known to be involved in signaling pathways of several integrin-mediated processes, such as cell adhesion, spreading, migration, and focal adhesion assembly (Lewis, J. M., et al., *J. Cell Biol.,* 1996; Ron, D., et al., *FASEB J.,* 1999; Huang, X., et al., *J. Cell Sci.,* 1998). Through the above results, the present inventors found that PKCδ activation is required for LG3- and Ln2-LG3-P2-mediated cell adhesion, spreading, migration, and neurite outgrowth in PC12 cells.

The activation of PKC results from the increase in intracellular diacylglycerol levels that is mediated by phospholipase C (PLC) activity, which is stimulated following the ligation of integrin β1. It was reported that treatment of PLC inhibitor U73122 leads to reduced α1β1 integrin-mediated PC12 cell adhesion (Vossmeyer, D., et al., *J. Biol. Chem.,* 2002). Therefore, the present inventors examined the effect of the PLC inhibitor U73122 on cell adhesion and spreading of PC12 cells.

PC12 cells were pretreated with U73122, an inhibitor for PLC, for 15 min at 37° C. and then seeded on plates coated with laminin (5 μg/mL), rLG3 (25 μg/mL), and Ln2-LG3-P2 (62.5 μg/mL) for 1 h or 3 h in serum-free medium.

As shown in FIG. 15, the PLC inhibitor, U73122 treatment reduced cell adhesion and spreading to rLG3 and Ln2-LG3-P2, suggesting that PLC activation, an upstream regulator of PKC, may be important in regulating integrin-mediated cell adhesion and spreading (FIG. 15).

What is claimed is:

1. A method of promoting cell adhesion, spreading, migration, or growth in vitro, wherein the cell expresses α3β1 integrin, the method comprising:
    treating the cell with a polypeptide or peptide, the polypeptide consisting of human laminin-2 α2 chain large globular (LG) 3 domain sequence SEQ ID NO:2), the peptide being an active peptide included in the human laminin-2 α2 chain large globular (LG) 3 domain sequence and consisting of one amino acid sequence selected from the group consisting of SEQ ID NOs: 1 and 37.

2. The method as set forth in claim 1, wherein the polypeptide or the peptide binds to α3β1 integrin.

3. The method as set forth in claim 1, wherein the polypeptide or the peptide regulates the intracellular location of protein kinase δ (PKCδ) through binding with α3β1 integrin.

4. The method as set forth in claim 1, wherein the polypeptide or the peptide induces tyrosine phosphorylation of PKCδ and focal adhesion kinase (FAK).

5. The method as set forth in claim 4, wherein the tyrosine phosphorylation of focal adhesion kinase (FAK) comprises tyrosine phosphorylation at amino acid position 397 (Tyr-397) in FAK.

6. The method as set forth in claim 1, wherein the polypeptide or the peptide promotes cell neurite growth.

7. The method as set forth in claim 1, wherein the cell is selected from the group consisting of PC12, normal African green monkey kidney fibroblast cell (CV-1), NIH/3T3, Schwann cells, normal human epidermal keratinocytes, normal human oral keratinocytes, and normal human dermal fibroblasts.

* * * * *